(12) United States Patent
Bogle et al.

(10) Patent No.: US 10,580,083 B2
(45) Date of Patent: Mar. 3, 2020

(54) RECORDING MEDIUM HAVING PROGRAM FOR FORMING A HEALTHCARE NETWORK

(71) Applicants: George E. Bogle, Lakeway, TX (US);
George M. Bogle, Phoenix, AZ (US)

(72) Inventors: George E. Bogle, Lakeway, TX (US);
George M. Bogle, Phoenix, AZ (US)

(*) Notice: Subject to any disclaimer, the term of this patent is extended or adjusted under 35 U.S.C. 154(b) by 73 days.

(21) Appl. No.: 15/956,285

(22) Filed: Apr. 18, 2018

(65) Prior Publication Data

US 2018/0240195 A1 Aug. 23, 2018

Related U.S. Application Data

(63) Continuation-in-part of application No. 14/453,382, filed on Aug. 6, 2014, now abandoned, which is a continuation-in-part of application No. 13/317,515, filed on Oct. 20, 2011, now abandoned.

(51) Int. Cl.
| | | |
|---|---|---|
| *G06Q 40/08* | (2012.01) |
| *G16H 10/60* | (2018.01) |
| *G16H 40/20* | (2018.01) |
| *G06Q 10/06* | (2012.01) |

(52) U.S. Cl.
CPC ............. *G06Q 40/08* (2013.01); *G16H 10/60* (2018.01); *G16H 40/20* (2018.01); *G06Q 10/06* (2013.01)

(58) Field of Classification Search
CPC ......... G16H 40/20; G06Q 40/08; G06Q 10/06
See application file for complete search history.

(56) References Cited

U.S. PATENT DOCUMENTS

| | | |
|---|---|---|
| 6,792,410 B1 | 9/2004 | Donovan et al. |
| 7,953,615 B2 | 5/2011 | Aquila et al. |
| 2002/0103680 A1 | 8/2002 | Newman |
| 2005/0171877 A1 | 8/2005 | Weiss |
| 2008/0120143 A1 | 5/2008 | Beauregard et al. |
| 2010/0063956 A1 | 3/2010 | McCallum et al. |
| 2010/0088114 A1 | 4/2010 | Carstens |

OTHER PUBLICATIONS

New England Journal of Medicine (Mar. 4, 1993; vol. 328 No. 9; pp. 621-627) article entitled "Geographic Variation in Payments to Physicians" by Welch, et al.

*Primary Examiner* — Jonathan Durant
(74) *Attorney, Agent, or Firm* — Matthews, Lawson, McCutcheon & Joseph, PLLC

(57) ABSTRACT

A centralized network can be established by contracting medical facilities and insurance providers, in which the medical facilities agree to waive all or a portion of a deductible amount owed as part of their contractual obligation with the network. The insurance providers agree to provide a credit of the premium to be paid by beneficiaries that use a contracted medical facility to receive a service for which the deductible amount is waived. The cost savings and increased revenue recognized by both medical facilities and insurance providers can enable claims to be re-priced while reducing transactional costs for all parties. A computer program can more efficiently and accurately categorize healthcare claims into in-network claims and out-of-network claims, in order to analyze non-network hospitals that may be good candidates for joining the centralized network.

17 Claims, 35 Drawing Sheets

Network Matching Criteria

Hospital NPI Match = Apply Part A Waiver
-OR-

| Hospital TIN | Hospital or DBA Name | Hospital Address | Hospital State | Hospital Zip | Apply Part A Waiver? |
|---|---|---|---|---|---|
| Y | Y | Y | Y | Y | Y |
| Y | Y | N | Y |  | Y |
| N | Y | Y | Y |  | Pend to Network |
| Y | N | N | N |  | N |
| Y | Y | Y | Y |  | Y |
| Y | Variation Up to 20 Characters | Y | Y |  | Y |
| Y | Y | N | N |  | Y |
| Y | N | Y | Y | Y | Y |
| Y | N | N | Y | Y | Pend to Network |
| Y | N | N | Y | N | Pend to Network |

Figure 5

Contracted Hospital Receives Explanation of Benefit (EOB)

Sample Facility Financial Profile Report

| | MEDICARE | MEDICAID | COMMERCIAL/OTHER | TOTAL |
|---|---|---|---|---|
| Medicare Certified Beds | 633 (3) | | | |
| Average Daily Census | 74% | | | |
| PATIENT REVENUE: | (4) $728,676,932 | (5) $47,154,732 | (6) $1,671,538,320 | $2,447,369,984 |
| DISCHARGE COUNT: | (7) 11,209 | (8) 2,850 | (9) 21,016 | 35,075 |
| ALOS (DAYS): | (10) 5.4 | (11) 4.8 | (12) 4.6 | (13) 4.9 |
| ADC: | (14) 166.9 | (15) 37.7 | (16) 266.8 | (17) 471.4 |

*Data taken from hospital's most recent reporting period ending 06/30/2012 (HCRIS 10221 - 2010). (18)

| | | |
|---|---|---|
| Medicare Gross Revenue: | $728,676,932 | =(4) |
| Medicare Discharge Count: | 11,209 | =(7) |
| Gross Rev / Med Discharge: | $65,008 | =(4)/(7) |
| Net Revenue / Medicare Discharge: | $17,552 | |
| PERCENT OF TOTAL GROSS REV: | 30% | |
| | | |
| Inpatient Revenue: | $1,283,337,728 | (19) |
| Outpatient Revenue: | $1,164,032,256 | (20) |
| *Total Patient Revenue: | $2,447,369,984 | =(19)+(20) |
| Contractual Allowances: | ($1,797,571,200) | (21) |
| *Net Patient Revenue: | $649,798,784 | =Total Patient Rev+(21) |
| Total Operating Expense: | ($574,617,472) | (22) |
| Operating Income: | $75,181,312 | =Net Patient Rev=(22) |

*After applying contractuals, Net Patient Revenue of Total Patient Revenue is approximately: 27% =Net Patient Rev/Total Patient Rev

| | PROJECTED NEW ADMISSION COUNT: | 25 | 50 | 75 | 100 |
|---|---|---|---|---|---|
| A | Gross Value of Additional Admissions: | $1,625,205.04 | $3,250,410.08 | $4,875,615.12 | $6,500,820.16 |
| B | *Factored at 27% as described above: | $438,805.36 | $877,610.72 | $1,316,416.08 | $1,755,221.44 |
| C | Percentage Income increase: | 1% | 1% | 2% | 2% |

A = PROJECTED NEW ADMISSIONS COUNT*[Gross Rev/Med Discharge]
B = ▓▓▓ [A]*Factored % on B
C = [B] %/Operating Income

Figure 27

Facility Analysis Report

| FACILITIES | Austin, TX - 2012 AHD Reporting With 2012-2013 Admit Data Combined | | | | | | Network Covered Lives: 786: 11,370 787: 6,974 | |
|---|---|---|---|---|---|---|---|---|
| | Medical Center #1 (Med Rev 39%) | Medical Center #2 (Med Rev 34%) | Hospital #3 (Med Rev 62%) | University Medical Center #4 (Med Rev 14%) | Medical Center #5 (Med Rev 62%) | Rehabilitation Hospital #6 (Med Rev 70%) | Surgical Hospital #7 (Med Rev 24%) | Surgical Hospital #8 (Med Rev 25%) |
| Gross Medicare Revenue (Per AHD) | $1,455,592,951 | $721,049,546 | $293,385,085 | $187,988,503 | $28,362,617 | $23,089,599 | $21,217,085 | $18,352,342 |
| Total Discharges (Per AHD) | 18,805 | 9,168 | 2,760 | 2,391 | 445 | 825 | 269 | 163 |
| Average Gross Medicare Revenue Per Discharge | $77,405 | $78,649 | $84,550 | $78,623 | $63,736 | $27,987 | $78,874 | $112,591 |
| Total Network Admits | 404 | 267 | 9 | 47 | 23 | 5 | 20 | 5 |
| Total Network Admit Value at Each Facility | $31,271,447 | $20,999,152 | $761,038 | $3,695,299 | $1,465,933 | $139,937 | $1,577,477 | $562,955 |
| Total cost of Part A Waivers | $478,336 | $316,128 | $10,656 | $55,648 | $27,232 | $5,920 | $23,680 | $5,920 |
| Value of Total Network- Eligible Admits Elsewhere at Medical Center #2's Average per Discharge | $78,649 | | X | 780 | 780 | | $61,346,220 | |
| Total Part A Deductibles | $1,184 | | X | | | | $923,520 | |

Figure 28

Premium Credit Sample Letter

From ▇▇▇ to ▇▇▇

John Senior
111 Anystreet
Anytown, State 00000

▇▇▇▇▇▇▇ is pleased to provide you with a $100 certificate which may be used on your next premium due date!

The above named hospital has agreed to work with ▇▇▇▇▇▇▇ Insurance Company to help hold down the cost of hospital stays and the insurance premiums associated with them. As a ▇▇▇▇▇▇▇ policyholder, you may benefit from this arrangement when you are confined in a participating hospital.

You may use the $100 certificate below towards your next premium payment. Simply save the certificate and send it in with your premium notice for policy #▇▇▇▇, along with your check or money order for any remaining premium due. YOU MUST <u>RETURN THE $100 CERTIFICATE WITH YOUR PREMIUM NOTICE</u> TO RECEIVE CREDIT.

▇▇▇▇▇▇▇ remains committed to providing you with quality Medicare Supplement protection and the best customer service at the lowest price possible. We appreciate your business and look forward to serving you for many years to come.

Sincerely,

▇▇▇▇▇
President

Return this certificate with your next premium payment for $100 credit..

This savings is a result of your stay in a hospital, which has agreed to participate in the ▇▇▇▇▇ Network. Our nationwide network of hospitals is as close as your phone. Participating hospitals do change from time to time; to verify the participating hospitals(s) in your area, please call.

 Insurance Company

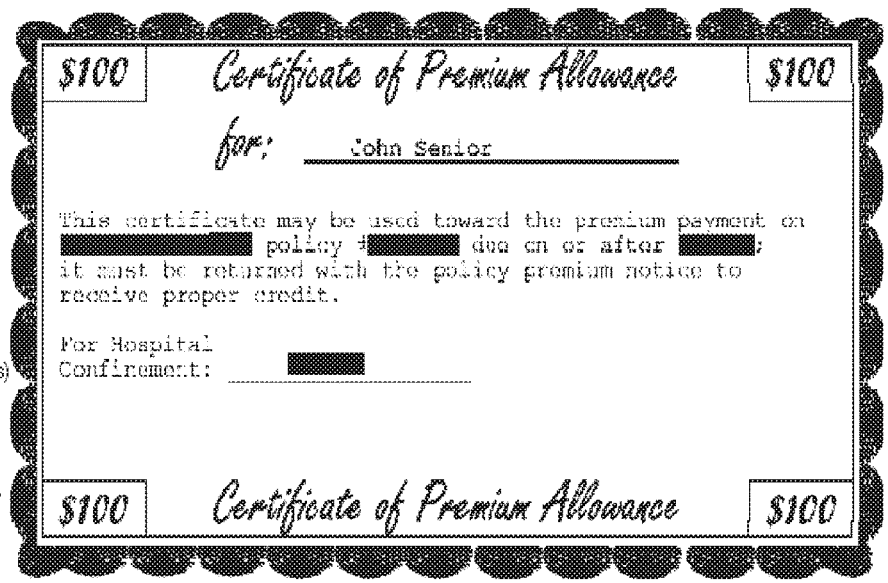

Figure 29

RECORDING MEDIUM HAVING PROGRAM FOR FORMING A HEALTHCARE NETWORK

CROSS REFERENCE TO RELATED APPLICATION

This application is a continuation-in part application of U.S. Non-Provisional patent application Ser. No. 14/453,382 filed on Aug. 6, 2014, which is a continuation-in part application of U.S. Non-Provisional patent application Ser. No. 13/317,515 filed on Oct. 20, 2011. The entireties of the prior non-provisional patent applications are incorporated herein, by this reference, for all purposes.

FIELD OF DISCLOSURE

The present disclosure relates, generally, to computer programs (stored on non-transitory computer readable recording mediums), methods and systems usable to categorize healthcare claims, reduce costs of healthcare transactions, and increase revenues. More specifically, embodiments described herein include computer programs, methods and systems for categorizing healthcare claims to reduce costs associated with insured patients, such as insurance premiums, and costs associated with insurance providers, such as deductible amounts, while increasing revenues to both medical facilities and insurance providers, by providing an incentive for patients to use contracted medical facilities and contracted insurance providers that have agreed to a system of practices and incentives.

BACKGROUND

In the United States, Medicare is administered by the government as a social insurance program. Medicare provides health insurance to citizens age sixty-five and older, as well as disabled individuals and those who meet other criteria. Medicare includes hospital insurance ("Part A"), which covers costs associated with hospital stays, use of skilled nursing facilities, hospice or home healthcare, and other similar expenses. Medicare also includes medical insurance ("Part B"), which covers most doctors' services, clinical and laboratory costs, home healthcare, outpatient services, and similar costs.

While Medicare can help covered individuals avoid catastrophic expenses, some Medicare plans only cover a portion (typically 80%) of expenses related to certain procedures, while the beneficiary is responsible for the remainder of the associated costs. Additionally, Medicare Part A includes a deductible amount (for example, $1,184 in 2013), which must be paid by the beneficiary. Further, any hospital stays that exceed sixty days in length incur a daily cost that must be paid by the beneficiary. And, any hospital stays that exceed ninety days require a greater daily cost to be paid and consume a limited number of "lifetime reserve days" allotted to each beneficiary. Once these lifetime reserve days are used, the full cost of each successive day of a hospital stay must be paid by the beneficiary. Similar policies, such as coinsurance for use of skilled nursing facilities, apply to other types of medical facilities.

Thus, even though Medicare covers the costs associated with a large portion of a beneficiary's healthcare transactions, beneficiaries remain burdened with considerable expenses not covered by Medicare, which can constitute a significant hardship for senior citizens and disabled individuals. As such, many private insurance companies offer supplemental insurance policies for Medicare beneficiaries, colloquially termed "Medigap" policies. While the premiums assessed by insurance providers for such policies are normally very costly, most Medicare supplemental insurance policies cover a patient's Medicare Part A deductible, as well as any portion of a healthcare expense not covered by Medicare. Many supplemental insurance policies also cover expenses associated with hospital stays that exceed the length covered by Medicare.

Many beneficiaries are unable to pay the costs associated with medical expenses not covered by Medicare, and hospitals are forced to write off these costs as uncollectable bad debts. As such, hospitals and other medical facilities strongly prefer treating patients covered by Medicare supplemental insurance policies due to the fact that revenue supplied by an insurance provider is not subject to the risk of becoming uncollectable in the same manner as an amount owed directly by a patient.

A need therefore exists for computer programs, systems and methods that can facilitate reduced premium expenses for beneficiaries of Medicare supplemental insurance policies, enabling a larger number of patients to obtain coverage by such policies.

A need also exists for systems and methods that increase hospital revenues, decrease transactional costs for hospitals and insurance providers, and reduce the number of patients not covered by a Medicare supplemental insurance policy. A need further exists for methods to more efficiently and accurately categorize healthcare claims into in-network claims and out-of-network claims, in order to analyze non-network hospitals that may be good candidates for increasing revenues and decreasing transactional costs.

Embodiments usable within the scope of the present disclosure meet these needs.

SUMMARY OF THE INVENTION

Example embodiments described herein relate, generally, to computer programs (stored on non-transitory computer readable recording mediums), systems and methods for reducing costs of healthcare transactions, including transactions between healthcare facilities and insurance providers that relate to Medicare claims, while the systems and method themselves are not part of Medicare or the Medicare payment process. A plurality of medical facilities (e.g., general or specialty hospitals, skilled nursing facilities, home healthcare providers, hospices, bariatric surgery facilities, chemical dependency facilities, long-term care facilities, physical rehabilitation centers, psychiatric facilities, residential treatment centers, sub-acute facilities, medical practitioners and groups thereof, and/or similar facilities) may be contracted to waive (e.g., subtract) at least a portion of an inpatient deductible for a group of insured patients. Concurrently, a plurality of insurance providers may be contracted to provide a premium credit to each insured patient that conducts an inpatient healthcare transaction with a contracted medical facility.

For example, contracted hospitals may agree to waive all or a portion of the Medicare Part A deductible for all Medicare patients who have Medicare supplemental insurance coverage that elect to use their facility. Concurrently, a provider of a Medicare supplemental insurance policy may agree to provide a patient with a $100 premium credit when the patient chooses to use a hospital that has agreed to waive all or a portion of the Medicare Part A deductible.

Medicare beneficiaries, who also have Medicare supplemental insurance coverage, are thereby provided with an incentive to use contracted hospitals to receive the premium credit while remaining free to use other Medicare-participating facilities as well. Thus, Medicare beneficiaries, who also have Medicare supplemental insurance coverage, avoid payment of the Medicare Part A deductible, which is a covered benefit through their contracted insurance provider, and may also receive reduced premium expenses through the premium credit. Additionally, Medicare beneficiaries, who also have Medicare supplemental insurance coverage, whether they use a contracted hospital or not, benefit from the savings resulting from the Part A deductible waivers because the contracted insurance providers use these savings to reduce the severity of premium rate increases for all policyholders.

While hospitals and other medical facilities would incur costs associated with waiving all or a portion of a deductible, medical facilities would see increased revenue through additional patients that would be incentivized to select a contracted medical facility. Additionally, incentivized patients that are covered by contracted insurance policies would provide a reliable source of revenue for medical facilities, reducing the number and the impact of bad debts and uncollectable patient balances. Demographic and/or financial data may be analyzed (e.g., via a computer-based analysis) to identify medical facilities suitable for contracting, and/or to determine whether contracting to waive a deductible amount would be profitable for a medical facility.

While contracted insurance providers would incur the cost associated with providing a premium credit to beneficiaries, insurance providers would also see increased revenue through additional enrolled beneficiaries incentivized by such premium credits, and cost savings associated with the waiver of all or a portion of the deductible amount by contracted medical facilities. Additionally, the increased revenue and reduced risk experienced by medical facilities can enable claims submitted to insurers to be re-priced, further reducing the costs borne by insurance providers. Similarly, the waiver of a deductible amount by contracted medical facilities can enable claims to be re-priced by insurers in a manner more profitable to medical facilities.

Thus, embodiments of the present disclosure provide for the management of a Medicare supplemental insurance network in which a healthcare provider waives all or a portion of the Part A deductible owed for services rendered, as part of its contractual obligation with the Medicare supplemental insurance network. In turn, a Medicare supplemental insurance provider receives a claim from the healthcare provider, re-prices the claim based on the Part A deductible waiver, and then issues payment to the healthcare provider based on the re-priced claim. The Medicare supplemental insurance provider can then issue a report to the Medicare supplemental insurance network for claims incurred, and may also issue a fee payment to the Medicare supplemental insurance network, which can be based on the amount saved and/or an amount of increased revenue experienced.

In an embodiment, a non-transitory computer readable recording medium stores a program to be executed on a computer. The program causes the computer to execute steps for forming a network for healthcare, comprising: electronically receiving items of information about a plurality of medical facilities, each item of information including at least a name associated with an identification number and/or an address belonging to one of the plurality of medical facilities; storing the items of information into a database; determining whether an item of information stored in the database is from an in-network medical facility of the plurality of medical facilities found within the network, or is from an out-of-network medical facility of the plurality of medical facilities found outside of the network, wherein the determining comprises: breaking down the name in the item of information into component words to determine whether each component word matches a word in a network name associated with one of the in-network medical facilities, and determining whether the identification number and/or the address associated with the name matches a network identification number and/or network address associated with one of the in-network medical facilities, wherein when the component words are at least 60% similar to the network name or its component words that are associated with one of the in-network medical facilities, and when the identification number and/or the address associated with the name is the same as the network identification number and/or the network address associated with the in-network medical facilities, the item of information is determined to be from an in-network medical facility; and when the component words are less than 60% similar to the network name or its component words associated with one of the in-network medical facilities, the determining further comprising breaking down the component words into component letters to determine whether the component letters match letters in the network name associated with one of the in-network medical facilities and determining whether the identification number and/or the address associated with the component letters matches the network identification number and/or the network address associated with one of the in-network medical facilities, wherein when the component letters are at least 90% similar to the letters in the network name and the identification number and/or the address associated with the component letters is the same as the network identification number and/or the network address associated with one of the in-network medical facilities, the item of information is determined to be from an in-network medical facility; building a thesaurus look-up table by adding to the thesaurus look-up table at least one of a synonym, acronym and misspelling of at least one of the component words used in names in the items of information, and mapping the at least one of the component words to the at least one of the synonym, acronym and misspelling, wherein the determining of whether each component word matches a word in the network name associated with one of the in-network medical facilities further comprises referring to the thesaurus look-up table to determine whether the component word matches at least one of the synonym, acronym and misspelling stored in the thesaurus look-up table, and wherein the determining of whether the component letters match the letters in the network name associated with one of the in-network medical facilities further comprises referring to the thesaurus look-up table to determine whether the component letters match letters of the at least one of the synonym, acronym and misspelling stored in the thesaurus look-up table, and wherein when the component words are less than 60% similar to the network name or its component words and the component letters are less than 90% similar to the letters in the network name associated with one of the in-network medical facilities, the item of information is determined to be from an out-of-network medical facility; and storing results of the determining.

The steps also include resolving whether a medical facility associated with an item of information that is determined to be from a medical facility that is outside of the network is to be included in the network, by assigning a value "X" to the medical facility, wherein the medical facility is included in the network when the value "X" is a positive number, and "X" is determined by the equation: X=[(R+S)−(D*A)]/N wherein "X" represents a monetary amount, "R" represents revenue due to increased patient admissions, "S" represents a monetary value of a payment from an insurance carrier, "D" represents a monetary amount of a deductible payment that is waived, "A" represents an adjusted revenue amount, and N represents a total number of new patient admissions, and wherein "R" is calculated by the computer processor based on the computer processor's evaluation of: demographic data that predicts the number of medical facilities needed, financial data of the plurality of medical facilities to determine which revenue stream comes from each type of insurance accepted by the medical facilities, admission and discharge data to predict the number of insured patients within a geographic area, and physician data to apply a grade to physicians having admitting privileges.

The steps further include adding to the network a medical facility having a value "X" that is a positive number; waiving at least a portion of the deductible owed to the medical facility having a value "X" that is a positive number and that is added to the network, upon performance of the healthcare transaction by a member of a group of insured patients; providing a premium credit to the member of the group of insured patients upon performance of the healthcare transaction with the medical facility having a value "X" that is a positive number and that is added to the network; receiving a claim from the each respective member of the plurality of insurance providers; re-pricing the claim by subtracting the at least a portion of the deductible; and issuing the premium credit to the member of the group of the insured patients associated with the claim.

In an embodiment, the deciding step further comprises: identifying a first number of reported admissions for each medical facility that is not in the network; extrapolating, based on the identifying, a second number of the insured patients in order to predict a number of expected new patient admissions over a period of time at each medical facility that is not in the network; evaluating demographic data to determine at least one location associated with the number of reported admissions; evaluating financial data of each medical facility that is not in the network within said at least one location to determine a percentage of revenue associated with the group of insured patients; and analyzing at least one of the percentage of revenue, the number of insured patients, the demographic data, the financial data, and the number of reported admissions, to determine a prospective result.

In an embodiment, the extrapolating the second number of insured patients using the first number of reported admissions comprises multiplying the first number by an inverse of an expected number of admissions per year for the insured patient.

In an embodiment, wherein the expected number of admissions per year is approximately 0.26.

In an embodiment, the deciding step further comprises: identifying, based on census data, each medical facility that is not in the network within a market area; determining a percentage of revenue of each medical facility that is not in the network and that is associated with the group of insured patients; determining, for each medical facility that is not in the network, at least one of an admission count and an average length of stay, associated with the group of insured patients; and analyzing, for each medical facility that is not in the network, at least one of the percentage of revenue, the admission count, and the average length of stay, to determine whether the group of insured patients constitutes a loss leader for each medical facility that is not in the network.

In an embodiment, the steps further comprise subtracting said at least a portion of the deductible times an adjusted revenue amount from a sum of an expected revenue from increased admissions and a quantity of insurance payments to obtain a value.

In an embodiment, the steps further comprise comprising dividing the value by a number of expected new patient admissions.

In an embodiment, the physician data comprises at least one of services offered and admitting privileges from specialty physicians.

In an embodiment, the deciding step further comprises: identifying, based on a medical facility profile, revenue, discharge, average length of stay, and average daily census for each medical facility that is not in the network, a projected value for new admissions; and conducting, based on a plurality of facility profiles in a geographic area, a facility analysis based on a maximum projected number of network admits in area medical facilities.

In an embodiment, the deciding step further comprises: identifying a number of beneficiaries, claim payments, admissions, or combinations thereof, using data sets for at least one insurance provider in an area; and aggregating the data sets for a utilization report determining the most utilized medical facilities.

In an embodiment, re-pricing the claim further comprises re-pricing the cost of a policy based on a notification issued to the plurality of insurance providers.

In an embodiment, the program further causes the computer to identify at least one insurance provider that requires additional contracting of medical facilities, by conducting at least one of claims analysis history, disruption study, and census count.

In an embodiment, the program further causes the computer to periodically provide a list of in-network medical facilities to the insurance providers, periodically provide a list of insurance providers to an in-network medical facility, or combinations thereof.

In an embodiment, the program further causes the computer to request collection of a fee from each in-network medical facility, the plurality of insurance providers, or combinations thereof, wherein the fee is determined by at least one of an amount of increased revenue and an amount of decreased costs.

In an embodiment, the plurality of insurance providers comprises Medicare supplemental insurance providers, and the deductible comprises a Medicare Part A deductible.

In an embodiment, the plurality of medical facilities comprises at least one of a hospital, skilled nursing facility, home healthcare provider, hospice, bariatric surgery facility, chemical dependency center, long-term care facility, physical rehabilitation center, psychiatric facility, residential treatment center, sub-acute facility, medical practitioner, and group of medical practitioners.

In an embodiment, the network is invisible to the insured patients.

BRIEF DESCRIPTION OF THE DRAWINGS

So that the manner in which the above recited features, advantages and objects of the present invention are attained and can be understood in detail, a more particular description of the invention, briefly summarized above, may be had by reference to the embodiments thereof which are illustrated in the appended drawings.

It is to be noted, however, that the appended drawings illustrate only typical embodiments of this disclosure and are therefore not to be considered limiting of its scope, for the disclosure may admit to other equally effective embodiments.

FIG. 5 depicts a table showing whether to apply a Part A Medicare waiver for re-pricing a healthcare claim in accordance with an embodiment of the disclosed methods and systems.

FIG. 27 is a sample facility financial report conducted in accordance with the disclosed methods and systems.

FIG. 28 is a sample financial analysis report conducted in accordance with the disclosed methods and systems.

FIG. 29 is a sample premium credit letter delivered to a beneficiary in accordance with the disclosed methods and systems.

DETAILED DESCRIPTION OF THE EMBODIMENTS

Figure 1:
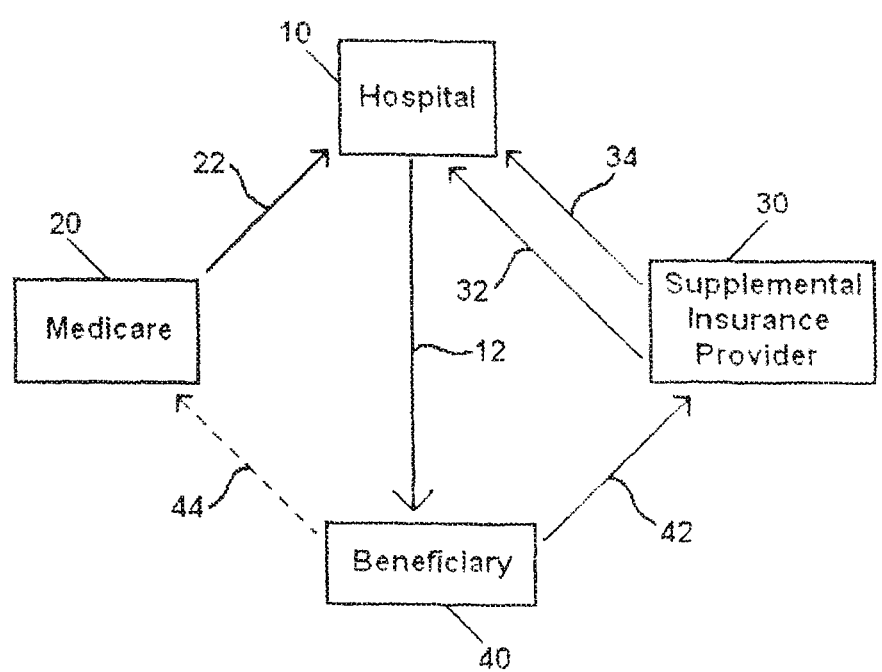
FIG. 1 depicts a prior art diagram showing the interactions between a hospital, Medicare, a supplemental insurance provider, and a beneficiary, in accordance with the disclosed methods and systems.

The following is a detailed description of example embodiments of the disclosure depicted in the accompanying drawings. The embodiments are examples and are in such detail as to clearly communicate the invention. However, the amount of detail offered is not intended to limit the anticipated variations of embodiments; on the contrary, the intention is to cover all modifications, equivalents, and alternatives falling within the spirit and scope of the present invention as defined by the appended claims. The detailed descriptions below are designed to explain such embodiments to a person of ordinary skill in the art.

Before explaining example embodiments of the present disclosure, it is to be understood that the present disclosure is not limited to the particular embodiments described herein and that the present disclosure can be practiced or carried out in various ways.

Embodiments usable within the scope of the present disclosure relate to computer-based systems and methods that utilize a healthcare network of contracted medical facilities and insurance providers, each of which have agreed to provide certain incentives that may cause patients to preferentially conduct healthcare transactions with contracted medical facilities, while permitting the patients to elect to use non-contracted medical facilities if desired.

An exemplary computer system for use with the disclosed methods and systems may include a processor, which is coupled to host bus coupled to cache memory. A host-to-personal computer interface (PCI) bridge is coupled to main memory, which includes cache memory and main memory control functions, and provides bus control to handle transfers among the PCI bus, processor, cache, main memory, and host bus. A PCI bus provides a standard interface for connecting peripherals, such as a local area network card. A PCI-to-industry standard architecture (ISA) bridge functions as a PCI target on the PCI bus to manage transfers between PCI bus and ISA bus, universal serial bus functionality, integrated drive electronics device functionality, power management functionality, a real-time clock, direct memory access control, interrupt support, and system management bus support. Peripheral devices and input/output devices can be attached to various interfaces (e.g., parallel interface, serial interface, infrared interface, keyboard interface, mouse interface, fixed disk, removable storage device) coupled to ISA bus.

Basic input/output system is coupled to the ISA bus, and incorporates the necessary processor executable code for a variety of low-level system functions and system boot functions. BIOS can be stored in any computer readable medium, including magnetic storage media, optical storage media, flash memory, random access memory, read only memory, and communications media conveying signals encoding the instructions (e.g., signals from a network). In order to attach the computer system to another computer system to copy files over a network, a local area network card is coupled to PCI bus and to PCI-to-ISA bridge. Similarly, to connect the computer system to an ISP to connect to the Internet using a telephone line connection, a modem is connected to a serial port and the PCI-to-ISA Bridge.

While the foregoing computer systems are capable of executing the disclosure described herein, these computer systems are simply examples of computer systems and user/computer systems. Those skilled in the art will appreciate that many other computer system designs are capable of performing the disclosure described herein.

Another embodiment of the disclosure is implemented as a computer program product for use within a device such as, for example, those above-described methods and systems. The program(s) of the computer program product defines functions of the embodiments (including the methods described herein) and can be contained on a variety of media including but not limited to: (i) information permanently stored on non-volatile or non-transitory storage-type accessible media (e.g., write and readable as well as read-only memory devices within a computer such as read-only memory, flash memory, CD-ROM disks readable by a CD-ROM drive); (ii) alterable information stored on writable storage-type accessible media (e.g., readable floppy disks within a diskette drive or hard-disk drive); and (iii) information conveyed to a computer through a network. The latter embodiment specifically includes information downloaded onto either permanent or even sheer momentary storage-type accessible media from the World Wide Web, an internet, and/or other networks, such as those known, discussed and/or explicitly referred to herein. Such data-bearing media, when carrying computer-readable instructions that direct the functions of the present disclosure, represent embodiments of the present disclosure.

In general, the routines executed to implement the embodiments of this disclosure, may be part of an operating system or a specific application, component, program, module, object, or sequence of instructions. The computer program of this disclosure typically comprises a multitude of instructions that will be translated by the native computer into a machine-readable format and hence executable instructions. Also, programs are comprised of variables and data structures that either reside locally to the program or are found in memory or on storage devices. In addition, various programs described hereto may be identified based upon the application for which they are implemented in a specific embodiment of this disclosure. However, it should be appreciated that any particular program nomenclature that follows is used merely for convenience, and thus this disclosure should not be limited to use solely in any specific application identified and/or implied by such nomenclature.

In a specific embodiment, a plurality of contracted medical facilities can agree to waive all or a portion of an inpatient deductible amount normally paid by a patient and/or by the patient's insurance provider. As a result, a plurality of contracted insurance providers may agree to provide a beneficiary with a premium credit (e.g., $100, issued as a payment certificate or notice of automatic credit toward payment of the next premium), on each occasion that the beneficiary completes an inpatient healthcare transaction at a contracted medical facility for which the deductible amount is waived. Consequently, patients may preferentially choose to use contracted medical facilities and contracted insurance providers, resulting in larger and more reliable revenue streams, and decreased costs for all parties involved. Optionally, the amount of premium credits received by a beneficiary within a selected time period can be limited, (e.g., a maximum of $600 in premium credits annually).

Medical facilities suitable for contracting can be identified in various manners. In an embodiment, admissions data can be received from a hospital or other type of medical facility. Specifically, the number of reported admissions for a geographic area (e.g., a state) can be identified, and this number can be used to extrapolate the number of insured patients within the geographic area. For example, based on historically reported data, a policyholder for a Medicare supplemental insurance policy experiences approximately 0.26 admissions per year. Using the inverse of this number (1/0.26=3.846), it can be estimated that each admission is representative of approximately 3.85 policyholders. Thus, for 100 admissions, the following equation could be applied: 100*(1/0.26)=100*3.846=384.6 policyholders per 100 admissions.

It should be understood, however, that the specific value used to extrapolate an estimated number of policyholders can vary based on geographic region, the type of insurance policy, patients, and/or medical facility being considered, changes or trends over time in historical data, and/or other similar factors. As such, use of the inverse of 0.26 is an exemplary embodiment based on current historical data relating to Medicare supplemental insurance policies; however, this value may change over time as medical, patient, and/or governmental practices change, or other values may be used with regard to different patient populations and/or insurance policies.

Demographic data can be analyzed to determine a specific area (e.g., a 3 or 5-digit zip code area within a state) within which admissions occurred. This data can be used to project the number of medical facilities needed to treat existing insured beneficiaries, and to account for future growth. A market analysis can then be conducted, e.g., using financial statements from one or more medical facilities in the specific area, to determine the percentage of revenue associated with a group of insured patients (e.g., Medicare beneficiaries).

In a further embodiment, medical facilities suitable for contracting can be identified by first identifying a market area using census data, and determining one or more medical facilities within that area. Market areas can be determined by identifying areas with a high population density and/or a large number of hospital admissions. In an embodiment, such an analysis can be performed using computer instructions adapted for such a purpose.

The payer mix of each medical facility can be analyzed to determine a percentage of revenue associated with a group of insured patients. For example, the financial data of a hospital or other medical facility can be analyzed to determine revenue streams from Medicare, Medicaid, and/or Commercial or Self-Pay. Following this financial analysis, the admission count and/or the average length of stay for one or more groups of insured patients can be determined.

A computer-based analysis (e.g., using a processor in communication with computer instructions) can be performed, thereby analyzing the one or more percentages of revenue determined, the admission count, the average length of stay, and/or other relevant factors, to determine whether a group of insured patients constitutes a loss leader. For medical facilities in which a group of insured patients constitutes a loss leader, the increased revenue generated by incentivizing patients from this group to utilize a specific medical facility will typically exceed the cost of waiving all or a portion of the deductible amount for such patients.

Medical facilities can further be graded based on various standards, such as services offered, admitting privileges from physicians (e.g., specialists) in the area, and/or other similar factors, thus enabling hospitals and/or other facilities to be ranked in order of desirability and/or the potential benefits of contracting through the present systems and methods.

For example, the benefits to a medical facility obtained through contracting and utilizing the present systems and methods can be summarized through the following equation:

$$X=[(R+S)-(D*A)]/N.$$

In the above equation, X represents the benefit to a hospital or other medical facility (measured in terms of new patient revenue), R represents revenue due to increased admissions (e.g., from additional patients incentivized by the waiver of a deductible amount and/or premium credits from an insurance provider), and S represents the value of a payment from an insurance carrier (e.g., payment of a claim by a Medicare supplemental insurance policy). D represents the amount of a deductible payment that is waived, A represents an adjusted revenue amount (based on retrospective payments through CMS), and N represents the number of new patient admissions.

Thus, when the sum of revenue received for increased admissions and the value of insurance payments exceeds the product of the amount of deductible waived times the adjusted revenue, a medical facility may constitute a loss leader and experience a financial benefit through the present systems and methods.

It should be understood that while various methods for determining whether contracting a medical facility will be suitable and/or profitable, any hospital or similar medical facility that accepts covered beneficiaries (e.g., Medicare patients) can be contracted and utilized in embodiments of the present systems and methods, independent of determinations made through demographic and/or financial data, without departing from the scope of the present disclosure.

Referring now to FIG. 1, a diagram depicting conventional interactions that occur between a hospital (10), Medicare (20), a supplemental insurance provider (30), and a beneficiary (40) is shown.

Typically, a hospital (10) provides a medical service (12) to a beneficiary (40). The beneficiary (40) obtains coverage from Medicare (20), provided that the beneficiary (40) is qualified to receive such coverage (e.g., due to age, disability, etc.). Under some circumstances, a beneficiary (40) must pay Part A premiums (44) to receive such coverage. For example, if the beneficiary (40) or a spouse has not undertaken forty quarters of Medicare-covered employment, Part A premiums (44) would be owed.

The beneficiary (40) can also receive coverage from the supplemental insurance provider (30) through payment of insurance premiums (42) thereto. Typically, the insurance premiums (42) assessed by a supplemental insurance provider (30) are costly; however, most Medicare supplemental insurance policies advantageously cover all or a portion of any medical cost not covered by Medicare (20).

Following provision of the medical service (12) to the beneficiary (40), the hospital (10) submits a claim to Medicare (20), responsive to which Medicare (20) provides a remittance (22) covering all or a portion of the cost of the medical service (12). Typically, the beneficiary (40) will be responsible for payment of a Part A deductible amount prior to receiving coverage from Medicare (20). Additionally the remittance (22) provided by Medicare (20) may only cover a portion (typically 80%) of the costs associated with the medical service (12), while the beneficiary (40) is responsible for payment of the remainder. Further, there exist certain medical services for which Medicare (20) will not provide coverage, such as the terminal portion of a hospital stay that exceeds 150 days.

As such, the supplemental insurance provider (30) pays the deductible amount (32) owed by the beneficiary (40) to the hospital (10). The supplemental insurance provider (30) also pays a remittance (34) to the hospital (10) for any costs not covered by Medicare (20), or only partially covered by Medicare (20).

Thus, in the depicted diagram, the beneficiary (40) must pay costly premiums (42) to obtain supplemental insurance coverage. As a result, many beneficiaries cannot afford such coverage, or elect not to purchase such coverage. Beneficiaries not covered by a Medicare supplemental insurance policy can incur significant financial responsibility if medical care is needed, and many hospitals must write off uncollectable patient balances as a result. Costs associated with healthcare services are often increased to account for uncollected debts.

The supplemental insurance provider (30) must pay not only the remittance (34) for costs not covered by Medicare (20), but must also pay a costly deductible amount (32) ($1,132 in 2011). Thus, the premiums (42) assessed by the supplemental insurance provider (30) are often costly to cover these expenses.

Figure 2:
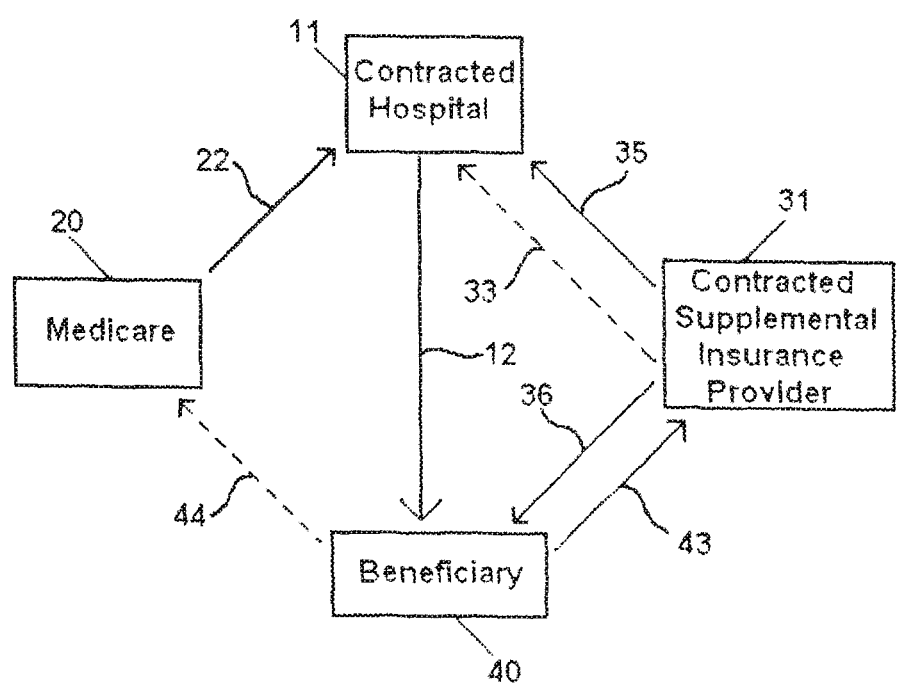
FIG. 2 depicts a diagram showing interactions between a contracted hospital, Medicare, a contracted supplemental insurance provider, and a beneficiary, in accordance with the disclosed methods and systems.

Referring now to FIG. 2, a diagram of an embodiment of a system usable within the scope of the present disclosure is shown, depicting the interactions between a contracted hospital (11), Medicare (20), a contracted supplemental insurance provider (31), and a beneficiary (40).

It should be noted that embodiments of the present systems and methods are not a part of Medicare and have no impact on the benefits due to a hospital or beneficiary under Medicare guidelines, nor on the obligations of a beneficiary to a hospital or to Medicare. As such, the interactions between the contracted hospital (11), Medicare (20), and the beneficiary (40) shown in FIG. 2 remain relatively unchanged from those shown in FIG. 1. FIG. 2 depicts the contracted hospital (11) providing a medical service (12) to the beneficiary (40). The beneficiary (40) may or may not be responsible for providing Part A premiums (44) to Medicare (20), as described previously. Responsive to receipt of a claim, Medicare (20) provides a remittance (22) to the contracted hospital (11), the remittance (22) covering all or a portion of the costs associated with the medical service (12).

Once contracted, the contracted hospital (11) agrees to waive all or a portion of the deductible amount owed by the beneficiary (40). As such, FIG. 2 depicts the contracted supplemental insurance provider (31) providing a partial or omitted deductible amount (33) to the hospital. FIG. 2 depicts the partial or omitted deductible amount (33) as a dashed line to illustrate that in various embodiments, no deductible amount may be owed (e.g., the contracted hospital may waive all of the Part A deductible amount), while in other embodiments, a partial deductible amount may be owed (e.g., the contracted hospital may waive a portion of the Part A deductible amount).

Due to the full or partial waiver of the deductible amount (33). the remittance provided by the contracted supplemental insurance provider (31) can be repriced. Thus, FIG. 2 depicts the contracted supplemental insurance provider (31) providing an adjusted remittance (35) to the contracted hospital (11).

Once contracted, the contracted supplemental insurance provider (31) agrees to provide a premium credit (36) to the beneficiary (40) for each transaction with a contracted hospital for which all or a portion of the Part A deductible amount is waived. Due to the provision of this premium credit (36), and additionally, due to the waiver of all or a portion of the deductible amount owed, the premiums assessed to the beneficiary (40) by the contracted supplemental insurance provider (31) can be modified. Thus, FIG. 2 depicts the beneficiary (40) providing a reduced premium (43) to the contracted supplemental insurance provider (31).

Therefore, while interactions between hospitals, beneficiaries, and Medicare remain unchanged, embodiments of the present systems and methods enable increased revenue and significant cost savings to contracted medical facilities and insurance providers, and to insured beneficiaries. Since the interactions between beneficiaries and hospitals and Medicare remain unchanged, the healthcare network processes (e.g., any contracts between medical facilities, insurance providers, and/or a third party network and the computer-implemented method for reducing costs of an inpatient healthcare transaction within the healthcare network including forming agreements, receiving claims, re-pricing, and generating premium credits) may remain invisible to beneficiaries as patients simply conduct healthcare transactions with medical facilities and insurance providers in the manner in which such transactions would normally occur.

Thus, in an exemplary embodiment, a beneficiary can receive medical care at a medical facility, and can experience cost savings while doing so, in the form of a premium credit provided by the patient's insurance provider. Additionally, it is contemplated that due to cost savings to insurance providers in the form of waived deductible payments and lower transactional costs, contracted insurance providers may be able to assess lower premiums to beneficiaries. The medical facility recognizes increased revenue through steerage of patients, who preferentially use contracted medical facilities due to the incentives offered, and through the guaranteed revenue stream provided by an insurance provider, minimizing the risk of uncollectable balances.

Figure 3:
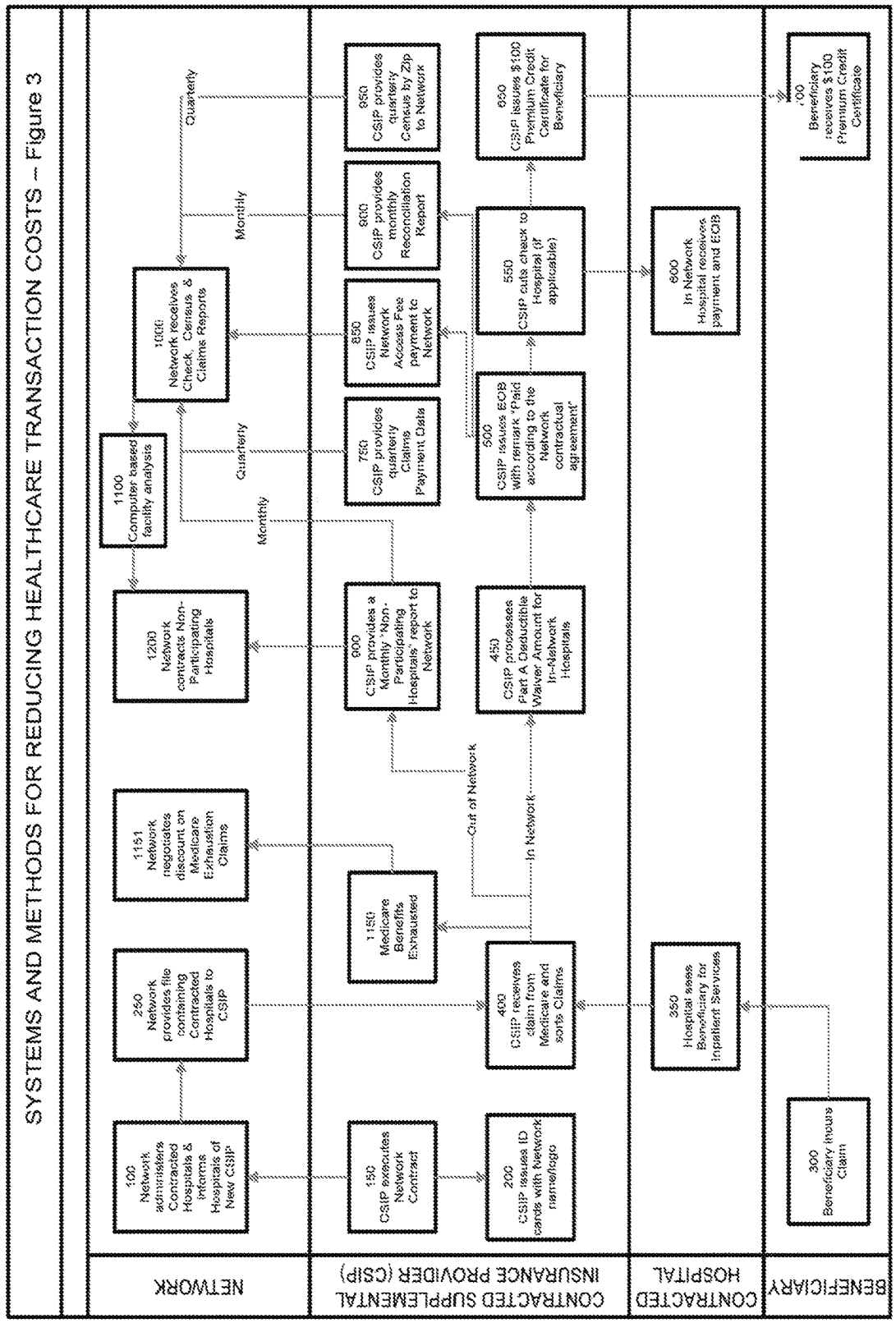
FIG. 3 depicts a diagram showing computer-based interactions among healthcare network participants in accordance with the disclosed methods and systems.

An exemplary embodiment of a computer-implemented network system is depicted with a high level overview in FIG. 3. The Network contracts with supplemental insurance providers (150) and facilities (1200) in order to provide for adjusted Part A Deductible waivers (450) issued as premium credits to CSIP beneficiaries (650) and compensated where applicable with direct payments from the CSIP to the facility (550). The Network also negotiates discounts on Medicare Exhaustion claims (1151). The Network then uses claims and facility gathered through the CSIP (1000) to analyze non-Network claims (1100) for possible expansion of the Network to non-participating facilities (1200). Each step of the exemplary embodiment will now be described in further detail as provided for in FIGS. 4-30 and TABLES 1-6.

Figure 19:
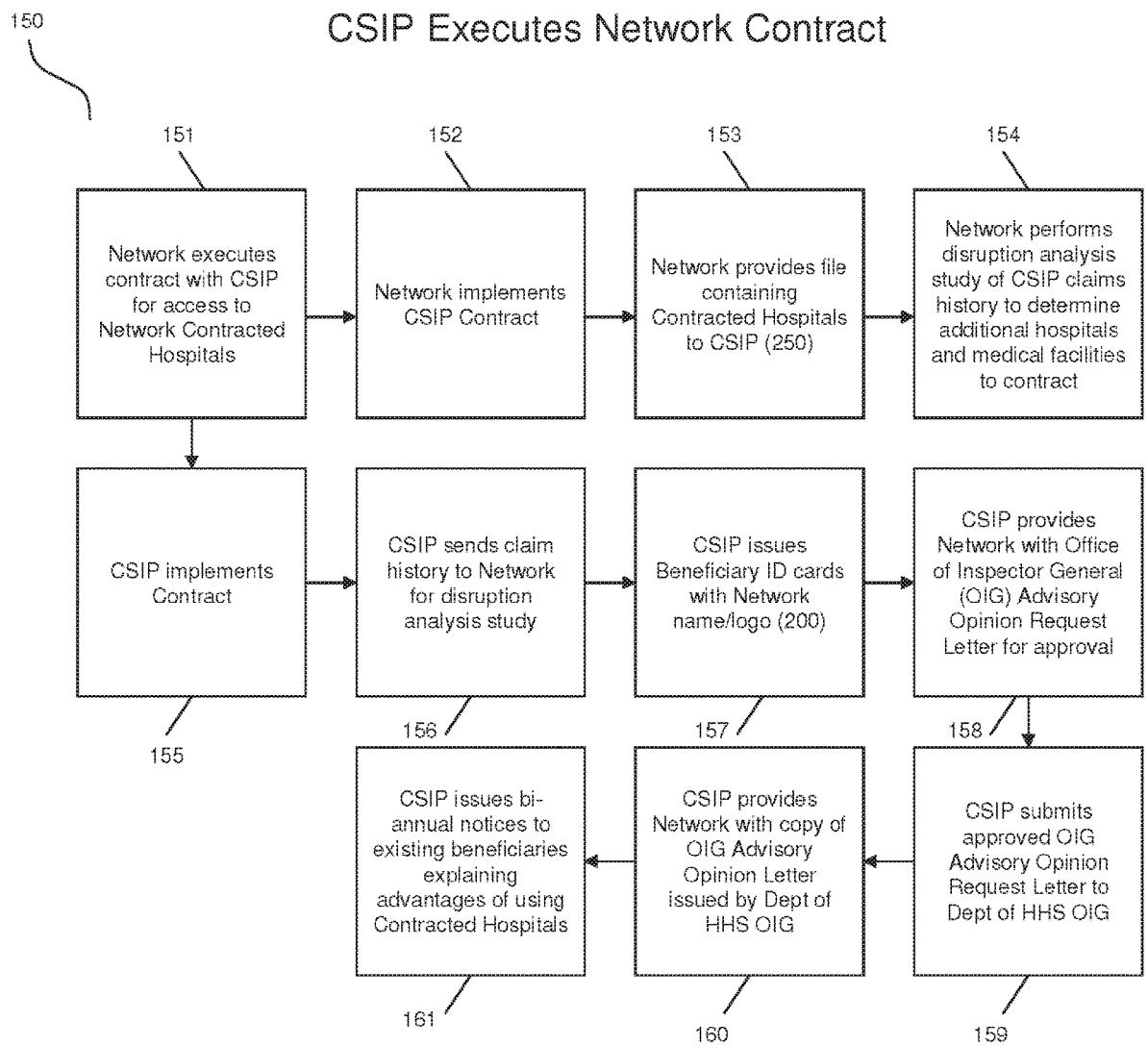
FIG. 19 depicts a flowchart of the CSIP executing the contracts underlying the Network in accordance with the disclosed methods and systems.

In an exemplary embodiment, insurance providers can be contracted following a review of historical data. Referring to FIG. 19, for example, a provider of a Medicare supplemental insurance policy can provide a 12-month Part A claims history (156), thus enabling projected access needs and historical access patterns to be analyzed. A disruption study can also be performed, in which any hospitals or other facilities listed in the 12-month Part A claims history are compared to existing contracted medical facilities (154). Following this analysis, a determination can be made regarding whether contracting the insurance provider in question will necessitate contracting additional medical facilities to ensure adequate patient access.

A supplemental geographical analysis of insurance providers' census counts by zip code of Medicare insurance policy insured member beneficiaries can be analyzed to determine network access ratio. An insurance provider sends Network census counts by zip code in electronic format (Microsoft Excel™, Microsoft Access™, ASCII or TXT delimited). Network generates a GeoAccess™ network adequacy report to determine access coverage for contracted medical facilities to insurance provider beneficiaries, typically within a 30-mile radius. Following this additional analysis, a determination can also be made regarding whether contracting the insurance provider in question will necessitate contracting additional medical facilities to ensure adequate patient access.

Figure 15:
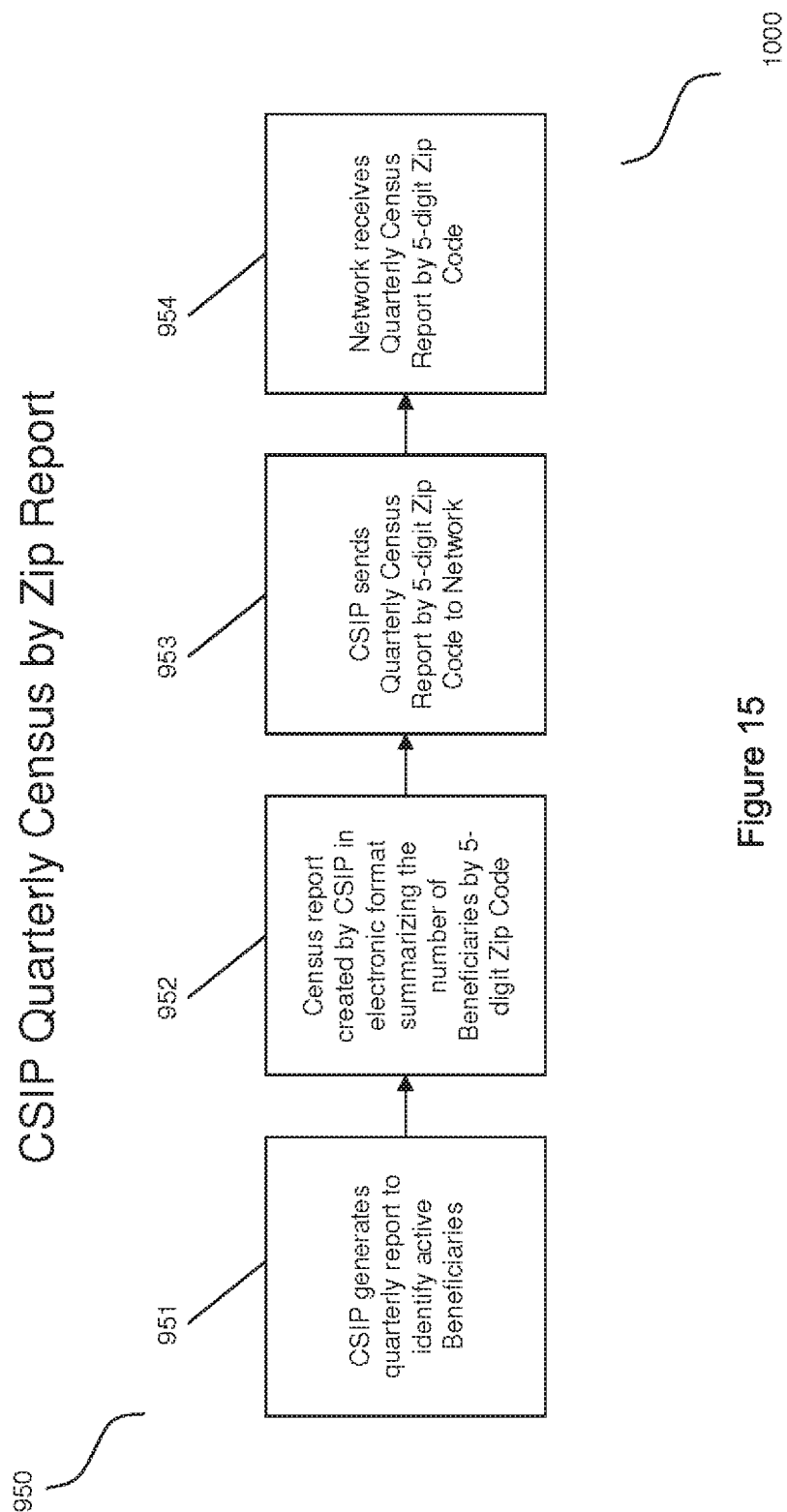
FIG. 15 depicts a flowchart of a quarterly census conducted by ZIP in accordance with the disclosed methods and systems.

In an exemplary embodiment, a Contracted Supplemental Insurance Provider (CSIP) provides a Network with quarterly census counts reports in electronic format (950). Referring now to FIG. 15, CSIP generates quarterly reports reflecting beneficiary counts by zip code (951). CSIP user logs in to eligibility system to access report menu for beneficiary counts. CSIP user enters quarterly timeframe for report selection with summarization by zip code the beneficiary count data requested. CSIP user accesses the reported data and populates it in Network's electronic report format (952) (Refer to TABLE 1 for report template). CSIP user uploads the quarterly beneficiary census count data on an established secure FTP site or sends to Network via secure email depending on CSIP reporting transmission set-up (953).

TABLE 1

Report Template for Primary Participant Count

| File Date (M/Y) | 5-Digit ZIP Code | Group Name | Group Number | Participant Count |
| --- | --- | --- | --- | --- |

Figure 16:
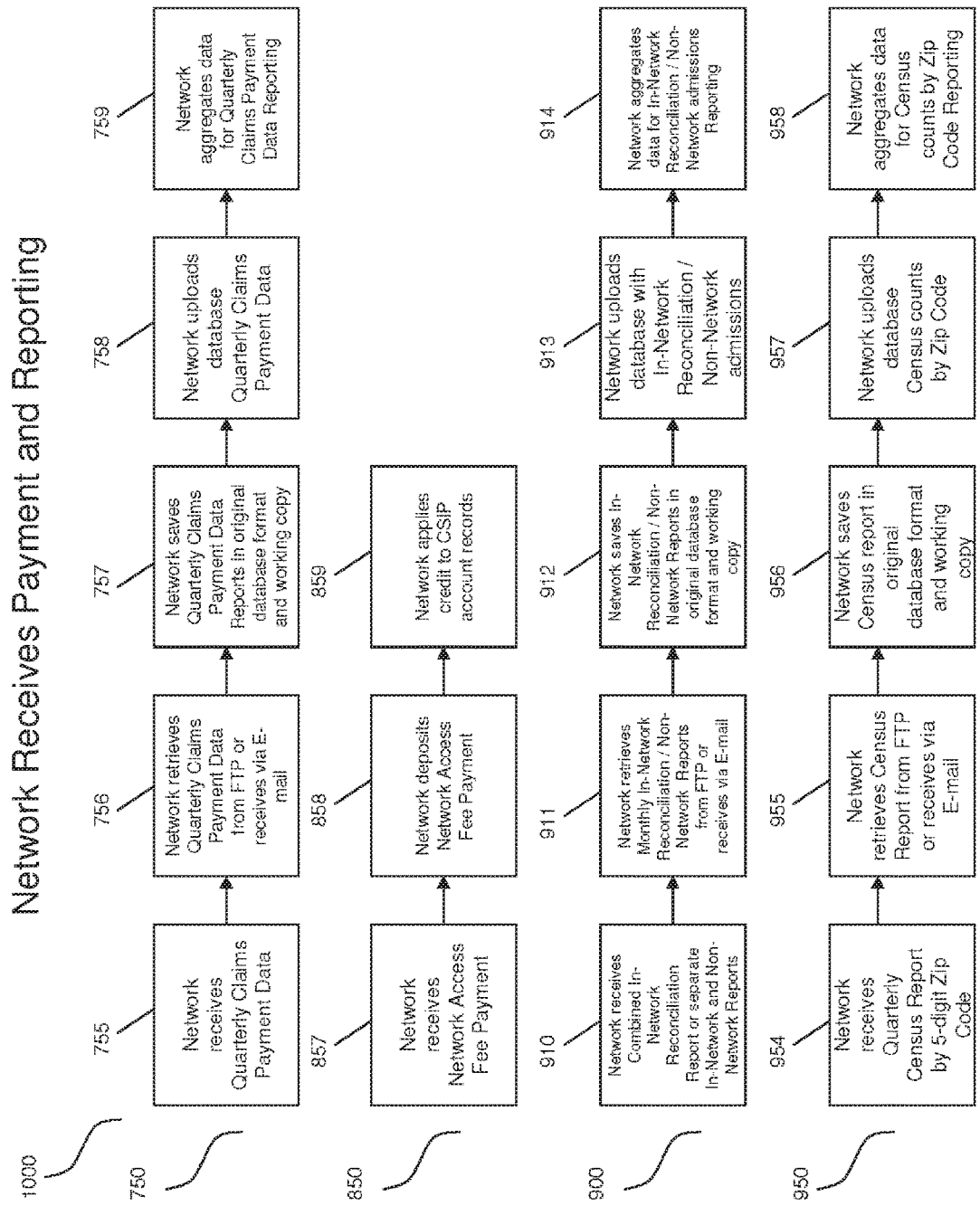
FIG. 16 depicts a flowchart of the payment and reporting process from the Network point of view, in accordance with the disclosed methods and systems.

Referring now to FIG. 16, Network receives quarterly beneficiary counts by zip code (954) by downloading the report from and established secure FTP site or by secure email (955). Network stores quarterly beneficiary count data reports in their original database format located on the network system (956). Network thus has a working copy of the quarterly beneficiary count data for processing (956). Network uploads quarterly beneficiary count data into database (957). Network aggregates data for alt CSIP submitted reports (958). Network users may now generate database server query reports on an ad-hoc basis for Network's medical facility marketing's use for developing the network of medical facilities resulting in executing contracts with medical facilities. The aggregated data is analyzed to determine the location of beneficiaries to the top utilized (paid) medical facilities. The aggregated data is reported to prospective contracting medical facilities to provide covered live data for the medical facility's specific geographic area.

As medical facilities and/or insurance providers are contracted, a list of all contracted facilities and/or providers can be maintained, and distributed to all contracted facilities and/or providers periodically (e.g., monthly) to assist beneficiaries in locating the nearest contracted medical facility. A readily available, network-accessible list can also be maintained, such as by providing a link to the list on the website of one or more insurance providers.

To facilitate transactions between contracted medical facilities and insurance providers, beneficiaries can be provided with identification cards that can be presented at a contracted medical facility at the time care is received, such that the healthcare transaction can be properly processed. For example, upon receipt of an identification card, a medical facility can waive all or a portion of a patient's Medicare Part A deductible, and transmits this information to the beneficiary's insurance provider, so that a premium credit can be provided to the beneficiary.

As part of a centralized network, contracted medical facilities and insurance providers can agree to various terms of operation. For example, in an embodiment, insurance providers can be obligated to complete medical bill processing and payment within thirty days of receiving a remittance. Similarly, medical facilities and/or insurance providers can be obligated to use certain re-pricing standards, use certain contractual language indicating waiver of a deductible amount when providing an explanation of benefits, or other similar terms of operation.

Contracted hospitals recognize increased revenue due to increased patient traffic, the patients being incentivized by the premium credits offered by insurance providers. Before contracting a hospital, an analysis can be performed to ensure that the revenue generated by increased patient traffic will exceed the cost incurred through waiving all or a portion of a deducible amount. Additionally, the increased revenue from patients covered by contracted insurance providers is not subject to becoming uncollectable in the same manner as a sum owed directly by a patient. Insurance providers recognize increased revenue through patients who preferentially use contracted insurance providers due to the incentives offered, through the waiver of deductible amounts, and through the ability to reprice claims due to the cost savings experienced by both medical facilities and insurance providers.

Figure 4A:
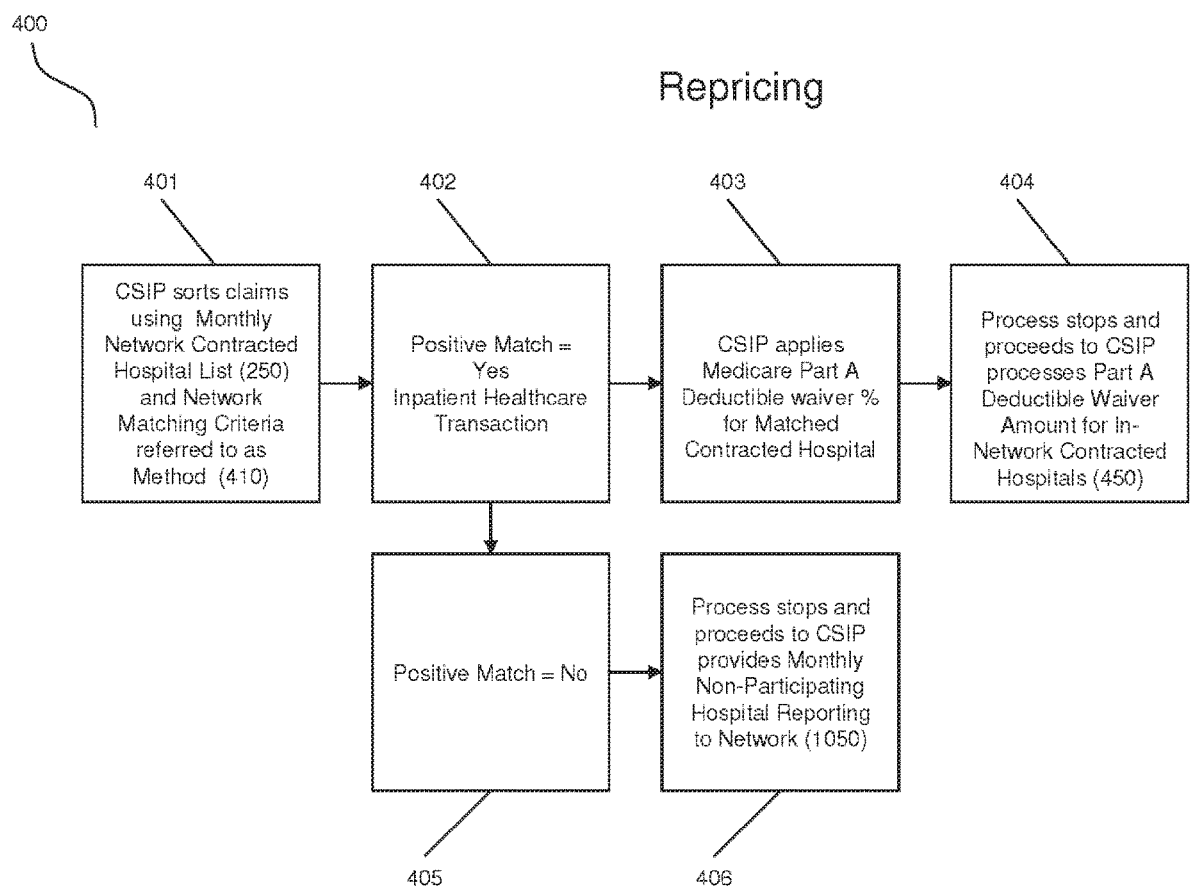
FIG. 4A depicts a diagram showing re-pricing of a healthcare transaction, and in particular, a healthcare claim within the healthcare network, in accordance with an embodiment of the disclosed methods and systems.
Figure 14:
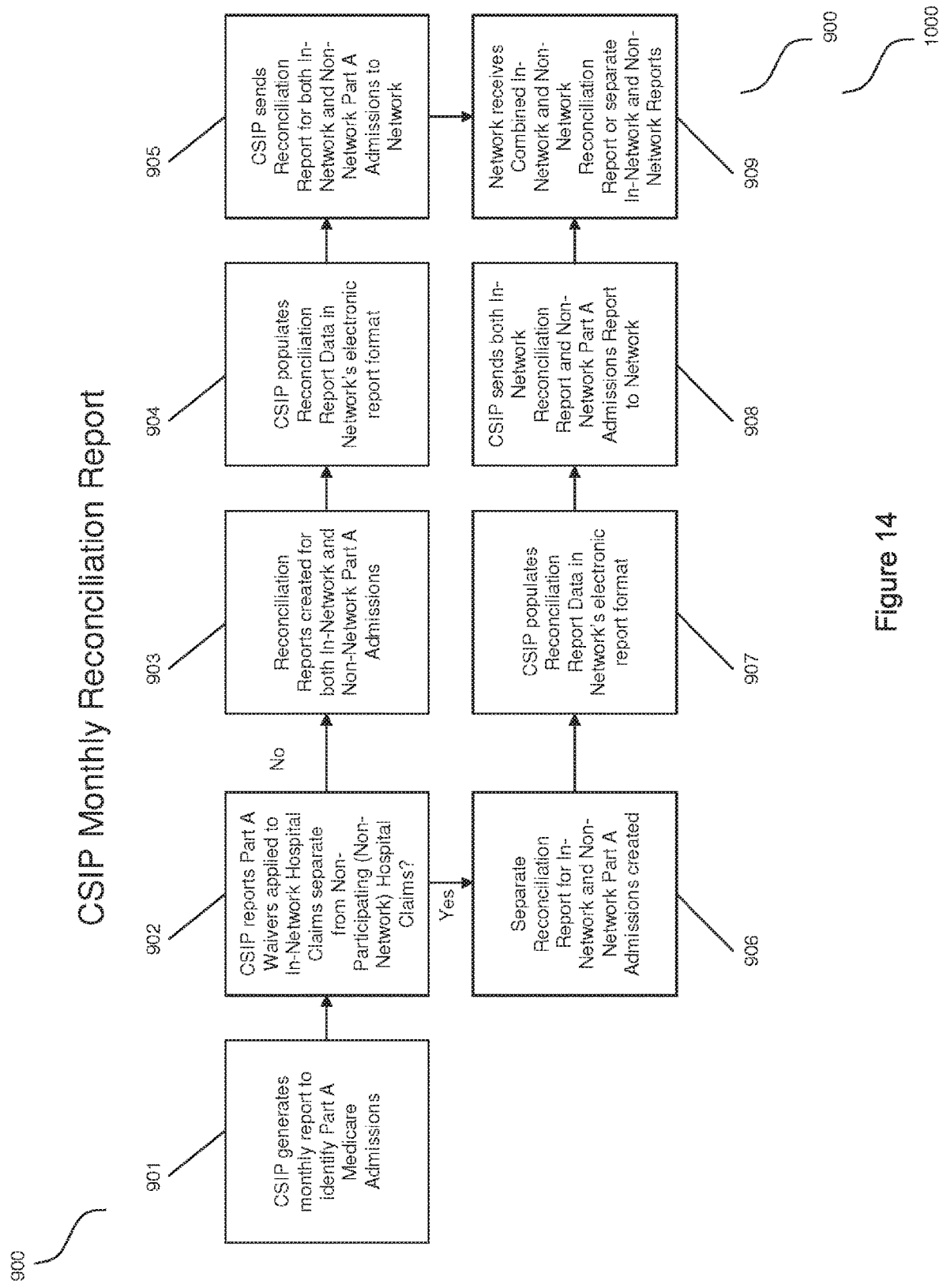
FIG. 14 depicts a flowchart of a monthly reconciliation process undertaken by the CSIP in accordance with the disclosed methods and systems.
Figure 17:
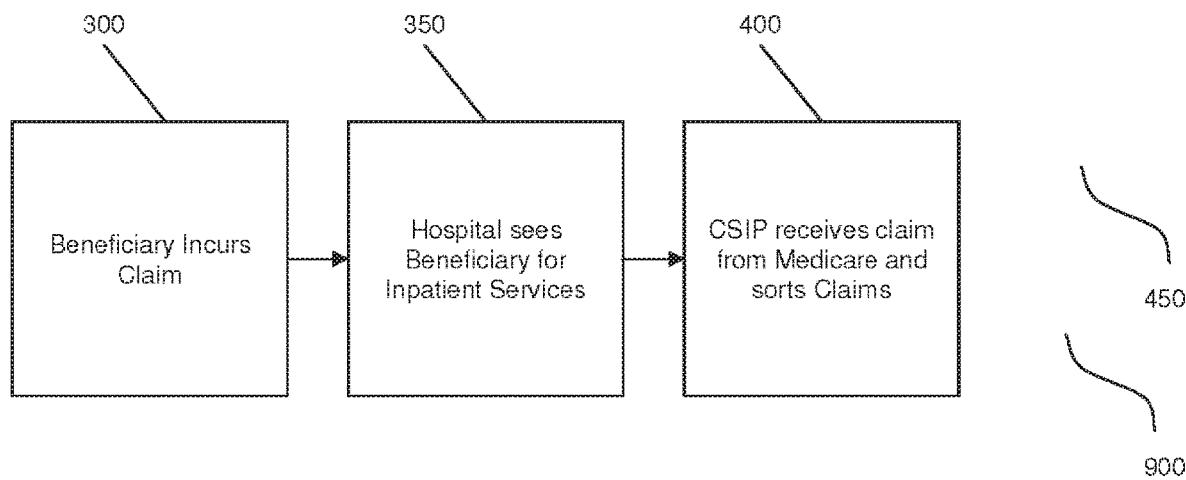
FIG. 17 depicts a flowchart of a beneficiary initiating the claims process in accordance with the disclosed methods and systems.

In an exemplary embodiment, referring now to FIG. 17, a beneficiary incurs a healthcare claim (300) and hospital renders care to beneficiary for inpatient services (350), upon discharge of a patient and completion of a hospital's billing process, a contracting hospital can send a bill to Medicare for processing. After receiving remittance and an explanation of benefits from Medicare, the remittance can be provided to a contracted provider of the patient's Medicare supplemental insurance policy for processing (400). At this time, the claim can be repriced by the insurance provider, or alternatively, a third party (e.g., a representative of the network of contracted medical facilities and insurers) can reprice the claim, such as through use of a computer-based analysis or similar algorithm as illustrated in FIG. 4A. Additionally, the claim is logged for use in the reconciliation process (900) as illustrated in FIG. 14, to be described later.

Referring now to FIG. 4A, Contracted Supplemental Insurance Provider (CSIP) sorts claims (401) within its system using the monthly Network Contracted Hospital listing provided to CSIP by Network in an electronic format, including, but not limited to Microsoft Excel™, fixed width .dsk, fixed width .txt, comma delimited .csv, ASCII delimited format (250). One method for sorting claims includes the use of network matching criteria which is more fully described in FIG. 5.

In an embodiment, the CSIP claims examiner accesses the claims adjudication system with secure username/password for manual claims processing. Medicare Part A deductible inpatient claims are flagged individually as claims received or queued to a file for claims examiner review. The CSIP claims examiner identifies the hospital billing for inpatient services rendered and cross references the Network Contracted Hospital listing by accessing the supplied electronic listing from the Network or stored data which is uploaded monthly by the CSIP. The Network Matching Criteria more fully described in FIG. 5 is one way for the claims examiner to determine if the hospital billing the claim is a Network Contracted Hospital.

In an embodiment with systematic claims processing, Medicare Part A deductible inpatient claims are flagged based on bill type, diagnosis-related group (DRG), and/or dates of service as claims are received from Medicare and uploaded in the CSIP's claim adjudication system.

In the exemplary embodiment shown in FIG. 5, CSIPs initiate the sort process (401), predominantly using the hospital's NPI (National Provider Identifier) determine a Network Contracted Hospital match. Additional matching criteria used by CSIPs may include a combination of hospital TIN (Tax Identification Number), hospital name or d/b/a name, hospital address, city, state, or zip code (411-419). Claims that apply to matching criteria 413, 418, and 419 are pended by the CSIP for confirmation of Contracted Hospital status. The process searches facility records through, for example, a proprietary AS/400 service provider, and provides a response to the CSIP indicating in-network or out-of-network status.

Referring now back to FIG. 4A, the CSIP proceeds with repricing the claim as in-network (402) or out-of network (405). For a matched in-network claim, the CSIP applies the Medicare Part A Deductible waiver % (403) and proceeds to process the claim with the Part A Deductible amount waived (404), (450). For an unmatched non-network claim, the CSIP proceeds to process the claim without a Part A Deductible waiver amount (406), (1050).

Figure 4B:
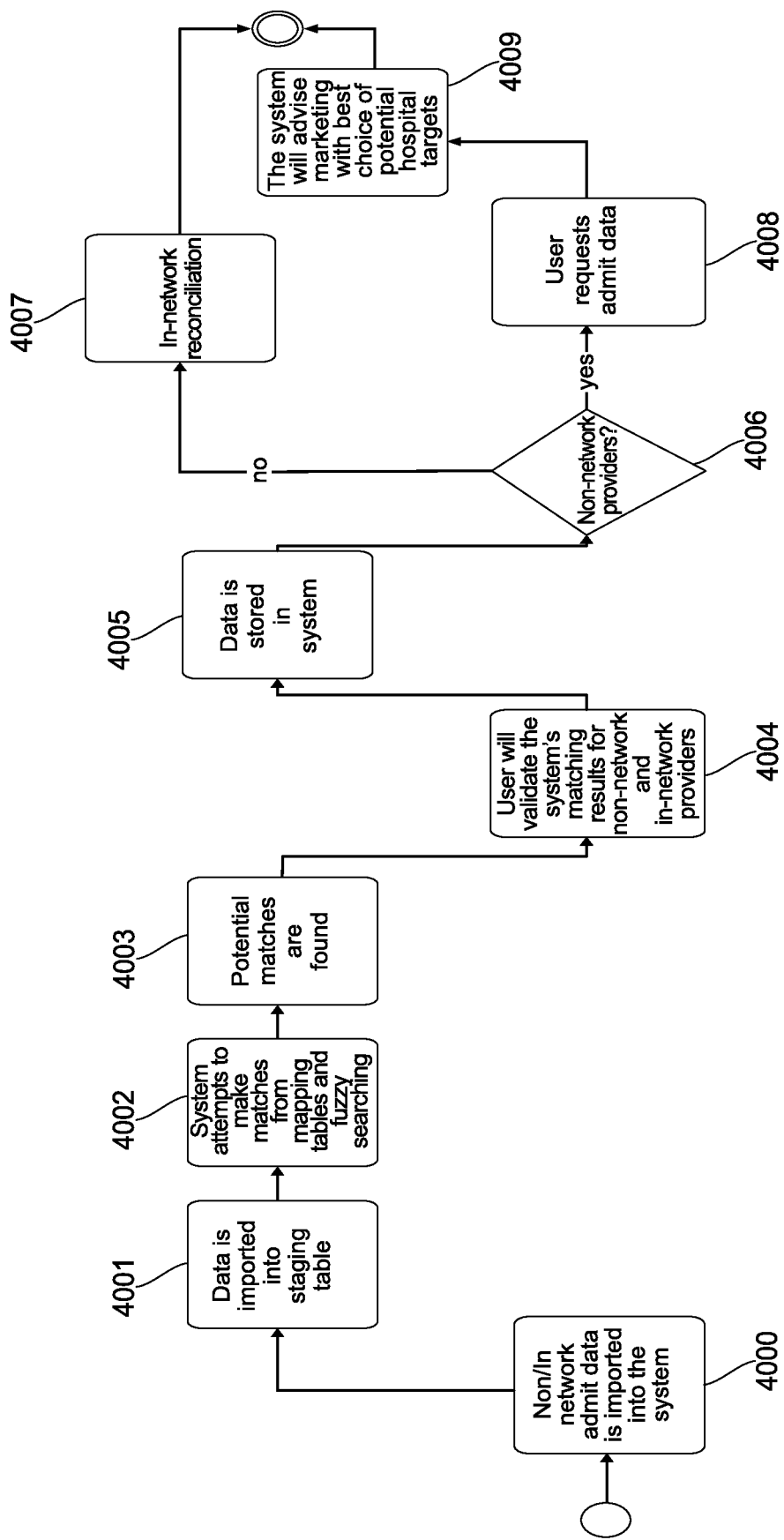
FIG. 4B depicts a preferred embodiment of a process for sorting and categorizing healthcare claims.

FIG. 4B depicts an alternative, preferred way to determine if the hospital billing the claim is a Network Contracted Hospital. The process depicted in FIG. 4B may be executed by a computer program that is stored on a non-transitory computer readable recording medium, such as write/readable and read-only memory devices within a computer, including a read-only memory and a flash memory, as discussed above. Other examples of non-transitory computer readable recording mediums include, as discussed above, a CD-ROM disk readable by a CD-ROM drive, readable floppy disks within a diskette drive or hard-disk drive, and portable storage devices that may be connected to a computer via a USB port. In other embodiments, the computer program may be conveyed to the computer through an Internet network. The computer program may contain codes and instructions that are executed on a computer to make the computer perform functions.

In the process executed by the program, administrative data, such as healthcare claims described herein, are imported (4000) from medical facilities, such as hospitals and doctor offices, and stored in a database (4001), such as in a table similar to the one shown in FIG. 5. The medical facilities may be any of the healthcare entities discussed herein. The administrative data may imported as items of information which are each from, or related to, a medical facility. The items of information may be related healthcare claims as described herein, and should include at least a name associated with an identification number and/or a mailing address belonging to one of the plurality of medical facilities. The identification number may be the TIN (Tax Identification Number) of the medical facility, or the NPI (National Provider Identifier) of the medical facility. In another embodiment, the identification number may further be another type of identification number of the medical facility.

Figure 4C:
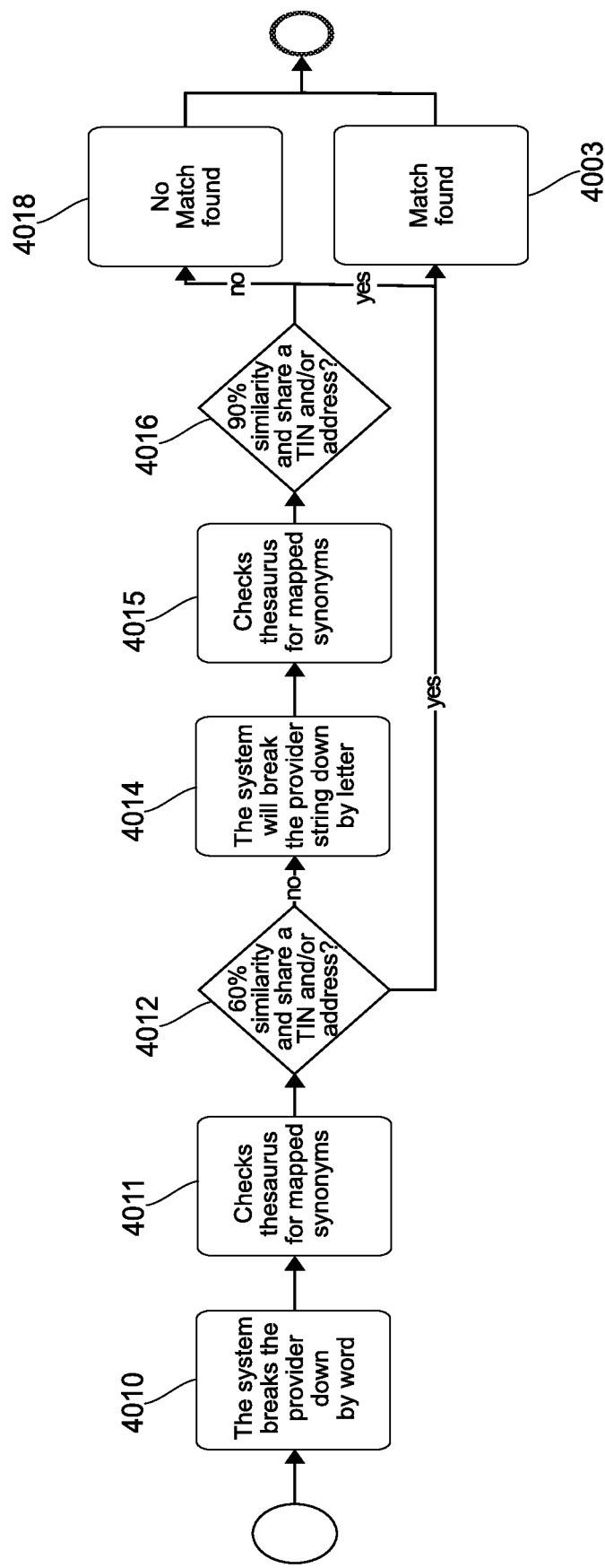
FIG. 4C depicts further aspects of the embodiment in FIG. 4B.

The process then proceeds to a matching procedure (4002) in which the items of information are searched to determine whether an item of information stored in the database id from, or belongs, to a Network Contracted Hospital (an "in-network medical facility") or is about a non-Network Contracted Hospital (an "out-of-network medical facility"). The matching procedure (4002) is explained in further detail with respect to FIG. 4C, and may be referred to as a "fuzzy" searching or "fuzzy matching". As shown in FIG. 4C, the matching procedure begins by having the program break down (e.g., separate) the name in the item of information by word into component words (4010) to determine whether each component word in the name matches with a word in a name of an in-network medical facility. The names of the in-network facilities may be stored on a list of in-network medical facilities. Those names may be referred to as "network names". The program also determines whether the identification number (e.g., the TIN or NPI) and/or the mailing address associated with the name that is broken down matches with an identification number and/or the mailing address of an in-network facility. For instance, the program may check identification numbers and/or the mailing addresses on a list of in-network medical facilities. The identification number (e.g., the TIN or NPI) and the mailing address provide an extra layer of assurance that the item of information having a name that closely resembles a name on the list of in-network medical facilities indeed is from, or belongs to, an in-network medical facility, e.g., an in-network medical facility that is on the list.

In determining whether the component word or words in the name of the item of information matches with a word in the network name of an in-network medical facility, the program may check a thesaurus look-up table (4011) to determine whether the component word or words in the name match with one of a synonym, acronym and/or misspelling of the component word or words in the thesaurus look-up table. For example, the thesaurus look-up table may include "hsptl" as an acronym or misspelling of the word "hospital". In addition, the thesaurus look-up table may include the words "medical center" as a synonym for the word "hospital". The thesaurus look-up table can thus increase the possibility of a true match between the component word or words in the name of the item of information and a word in the network name of an in-network medical facility when one of the component words in the name of the item of information is misspelled, is abbreviated, is incomplete or is missing from the name.

The program can build the thesaurus look-up table over time by adding to the thesaurus look-up table synonyms, acronyms and/or misspellings of a component word or words used previously in the names in the items of information, or that are entered by a user, and mapping the synonyms, acronyms and/or misspellings to the component word or words. The thesaurus look-up table may have a simple grid-like format with the component word or words used in a name in one column, and each of the synonyms, acronyms and/or misspellings of the component word or words in a separate column, but in the same row as the component word or words. The thesaurus look-up table can be built with user input, such as the user manually entering synonyms, acronyms and/or misspellings of the word or words into the table. Alternatively, the program itself can build the thesaurus look-up table by adding potential synonyms, acronyms and/or misspellings that appear to correspond to the component word or words, and that may later be confirmed by user. As the thesaurus look-up table is built, the program can become more effective at matching the component word or words in the name of a medical facility with the word or words in the name of an in-network medical facility. This is because the program learns, new synonyms, acronyms and/or misspellings as they are added over time. The more synonyms, acronyms and/or misspellings that are added to the thesaurus look-up table, the smarter the program can be. The functioning of the program can thus be improved by being more efficient and effective over time. The thesaurus look-up table improves on conventional look-up tables and "all-or-nothing" computer searching techniques that search for only exact matches of words and/or names.

In step (4012) of the process, it is determined whether the component word or words in the name that is broken down is at least 60% similar to a word or words of a network name of an in-network medical facility (e.g., by checking the list of in-network facilities), and whether the identification number and/or the mailing address associated with the name that is broken down is the same as the network identification number and/or the mailing address of an in-network medical facility. If so, the item of information is determined to be from or about a medical facility that is in the network (4003). It is noted that the step (4012) determination may use the synonyms, acronyms and/or misspellings from the thesaurus look-up table in step (4011) as the component word or words in the name that is broken down, such that it is determined whether a synonym, acronym and/or misspelling of a word or words in the name is at least 60% similar to a word or words of a network name of an in-network medical facility.

If the component word or words (or a synonym, acronym and/or misspelling of a word or words) in the name that is broken down is less than 60% similar to a word or words of a network name of an in-network medical facility (e.g., by checking the list of in-network medical facilities)s, the process proceeds to step (4014).

In step (4014), the program breaks down (e.g., separates) the component word or words of the name into component letters to determine whether each component letter in the name of the item of information matches with a letter in the name of in-network medical facility (e.g., a medical facility on a list). In addition, it is determined whether the identification number and/or the mailing address associated with the name that is broken down into component letters matches with the network identification number and/or the network address of an in-network medical facility. In step (4015), the program refers to again to the thesaurus look-up table to see if the component letters in the name in the item of information match with letters of any synonyms, acronyms and/or misspellings of the name in the thesaurus look-up table. The process then proceeds to step (4016), in which it is determined whether the component letters of the name that is broken down (or letters in the synonyms, acronyms and/or misspellings of the name) are at least 90% similar to letters in the network name of an in-network medical facility, and whether the identification number and/or the mailing address associated with the name that is broken down into component letters is the same as the network identification number and/or the network address of an in-network medical facility. If these two criteria are met, the item of information is determined to be from or belong to a medical facility that is in the network (4003).

On the other hand, if the component letters of the name that is broken down (or letters in the synonyms, acronyms and/or misspellings of the name) are less than 90% similar to letters in the network name on the list of in-network medical facilities, the item of information is determined to be about a medical facility that is not in the network (4018). Thus, in the process, when the component word or words (or the synonyms, acronyms and/or misspellings of the word or words) in the name that is broken down is less than 60% similar to the word or words of the name of an in-network medical facility, and the component letters of the name that is broken down (or letters in the synonyms, acronyms and/or misspellings of the name) are less than 90% similar to letters in the network name of an in-network medical facility, the item of information is determined to be from or belong to a medical facility that is not in the network (i.e., an "out-of-network medical facility") (4018).

The matching technique discussed herein improves on conventional "all-or-nothing" computer matching techniques that simply determine exact matches of words and/or names. As discussed herein, the computer program can match component words in a name that are at least 60% similar to the actual words of the network name to find a potential match. Moreover, the computer program can match component letters in a words or words of a name that are at least 90% similar to the letters of the actual network name to find a potential match. The potential match can be strengthened by matching the identification number and/or the mailing address of the medical facility in the item of information, and by utilizing the thesaurus look-up table. This multi-variable approach for matching claims to in-network facilities even when the medical facility name on the claim does not match exactly with the name of an in-network medical facility (e.g., that is on the list of in-network medical facilities), improves on previous conventional computer technology and functioning in the this art which relies only on exact matches of the name. Further, the thesaurus look-up table improves computer functionality by making the computer more efficient and effective at matching the component word or words in the name of a medical facility with the word or words in the name of an in-network medical facility, by finding potential matches with the use of synonyms, acronyms and/or misspellings. Further, the computer is subject to machine learning from the new synonyms, acronyms and/or misspellings that are added over time, and so each iteration of determination procedures becomes more effective. For instance, the probability of matching the name in a claim (item of information) to the network name of an in-network medical facility is increased for names in the claim that are misspelled, abbreviated, or incomplete.

Returning now to FIG. 4B, once a potential match is found (4003), the match can optionally be validated by a user (4004) before the matching results are stored (4005) in a database. The items of information from or belonging to in-network medical facilities are then separated (4006) from the items of information belonging to out-of-network medical facilities. Next, the items of information belonging to in-network medical facilities are logged (4007) for use in one or more of the reconciliation processes described herein. The items of information belonging to out-of-network medical facilities may optionally be requested by a user for further evaluation before proceeding to step (4009), where out-of-network medical facilities are analyzed to determine whether they are good candidates for joining the network as an in-network medical facility. That determination utilizes the equation $X=[(R+S)-(D*A)]/N$ and its associated processing, discussed above.

Figure 4D:
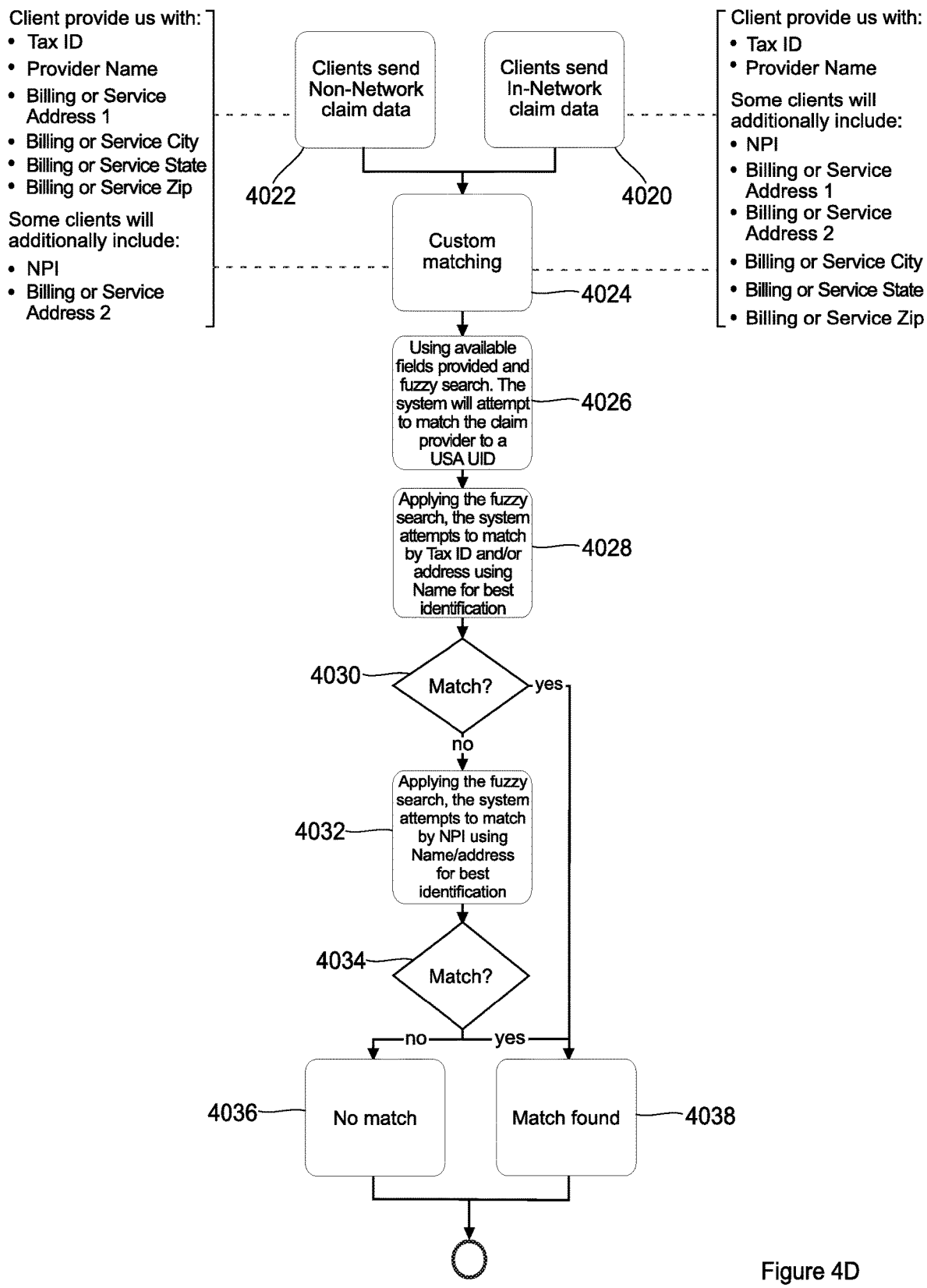
FIG. 4D depicts another embodiment of a process for sorting and categorizing healthcare claims.

FIG. 4D illustrates another embodiment of sorting and categorizing healthcare claims. In this embodiment, the process may be for matching Medicare claims. In the process, in-network claim data is entered at step (4020), and non-network claim data is entered at step (4022). The in-network claim data may include a provider name and a TIN (Tax Identification Number). The in-network claim data may further include an NPI (National Provider Identifier), one or more billing addresses, a billing or service city, a billing or service state, and a billing or service zip code. The non-network claim data may include a provider name, a TIN (Tax Identification Number), a first billing address, a billing or service city, a billing or service state, and a billing or service zip code. The in-network claim data may further include an NPI (National Provider Identifier) and a second billing address. The computer program implements a custom matching process (4024) that begins with a procedure to match the entered claim to a U.S.A. UID (Unique Identification Number) (4026). The computer program determines whether the TIN and any of the address information in the claim matches with a TIN and address information stored in a list or database. Additionally, the computer program may use the procedure discussed above with respect to FIG. 4B to break down a word or words of the provider name in the claim data, or to break down the word or words by letters, as an additional measure to ensure a proper match of the claim. If a match is found (4030), the match is confirmed at step (4038).

If a match is not found at step (4030), the computer program determines whether the NPI in the claim matches with an NPI stored in a list or database (4032). Additionally, the computer program may use the procedure discussed above with respect to FIG. 4C to break down a word or words of the provider name in the claim data, or to break down the word or words by letters, as an additional measure to ensure a proper match of the claim. The program may also break down the mailing address information by word or letter using the procedure discussed above with respect to FIG. 4C. If a match is found (4034), the match is confirmed at step (4038). Otherwise, it is determined that no match is found (4036). The results of the matching are stored in a database, as in the example discussed above, and medical facilities having the non-matching claims that are determined to be out-of-network may be further analyzed as discussed above.

Figure 6:
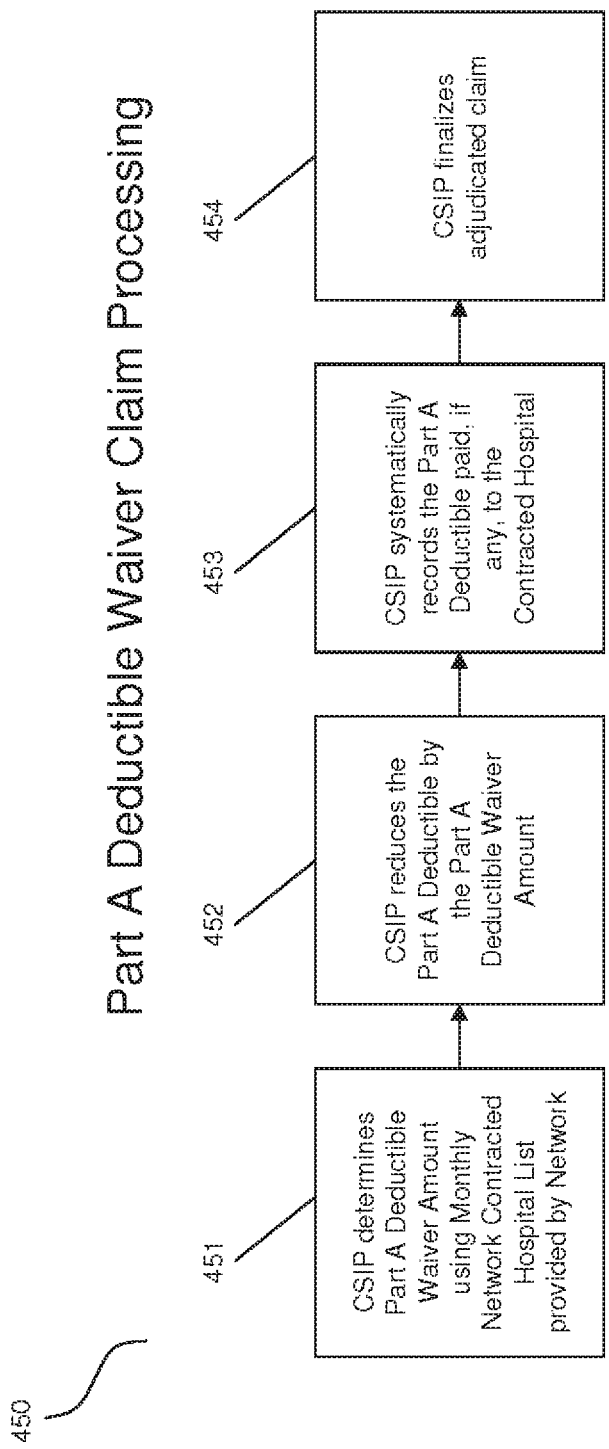
FIG. 6 depicts a flowchart showing the claim processing procedure as applied to a Medicare Part A waiver in accordance with the disclosed methods and systems.

Referring now to FIG. 6, once the Part A Deductible waiver amount is determined to be applicable to the claim being processed (451), the CSIP systematically, or through manual calculation by a claims examiner, reduces the Part A Deductible payable to the Contracted Hospital by the waiver amount (452). The CSIP records the Part A Deductible payable to the Contracted Hospital, if any (453). The claim is then finalized systematically or manually by the CSIP's claim examiner (454).

Figure 7:
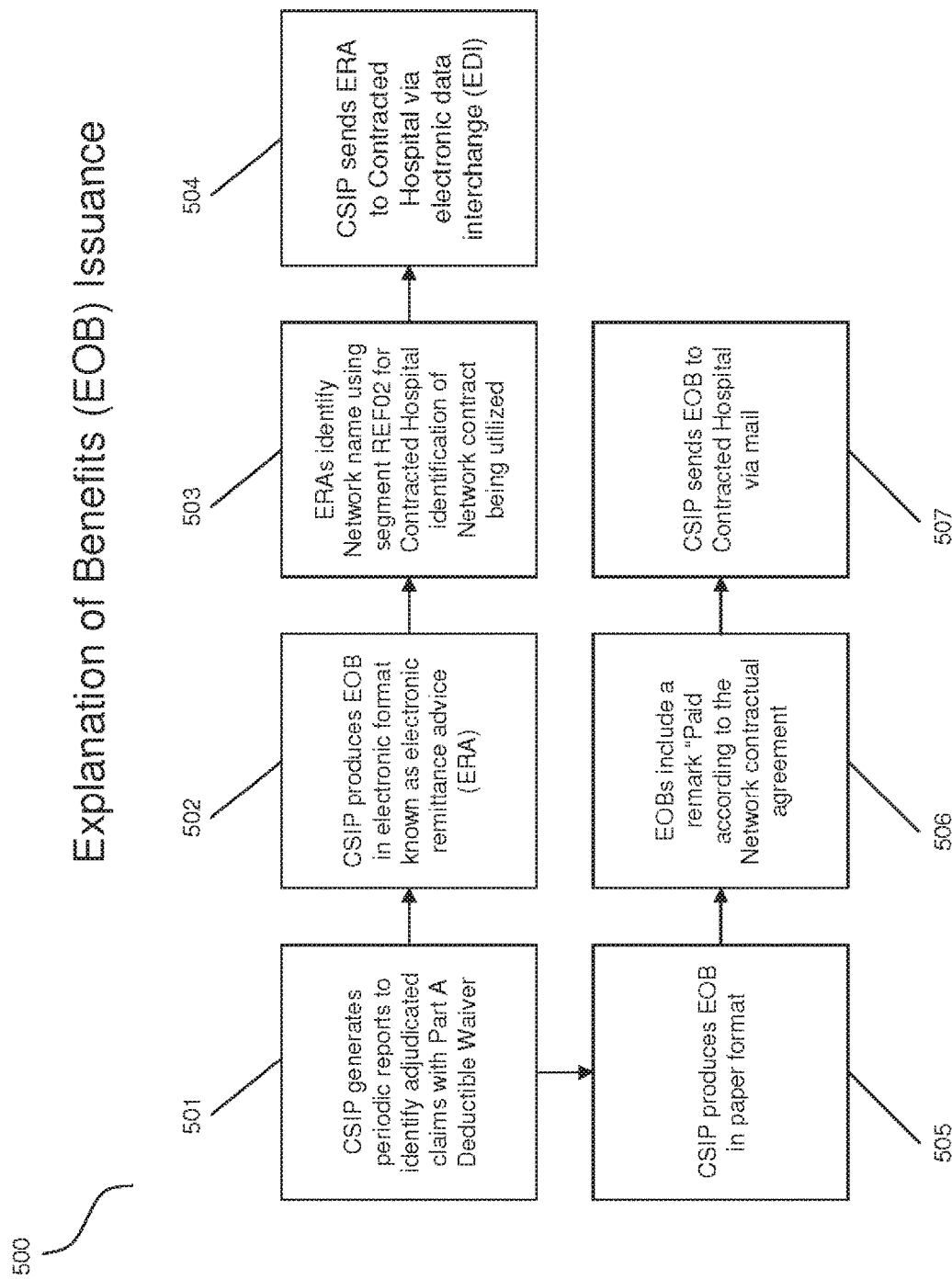
FIG. 7 depicts a flowchart showing the issuance of an Explanation of Benefits (EOH) statement in accordance with the disclosed methods and systems.

Referring now to FIG. 7, using generated system reports identifying adjudicated claims with Part A Deductible Waivers (501), the CSIP produces Explanation of Benefit letters (EOBs) in electronic format known as electronic remittance advice (ERA) (502). The CSIP identifies Network names using segment REF02 for Contracted Hospital identification of the Network contract being utilized (503). The CSIP sends ERAs to Contracted Hospitals via electronic data interchange (EDI) (504). For Contracted Hospitals not set up to receive ERAs electronically, the CSIP issues an explanation of benefits (EOB) in paper format (505). EOBs include a remark "Paid according to the Network contractual agreement" (506). The CSIP sends EOBs to Contracted Hospital by mail (507) with payment, if applicable, as checks are issued to Contracted Hospitals (550).

Figure 8:
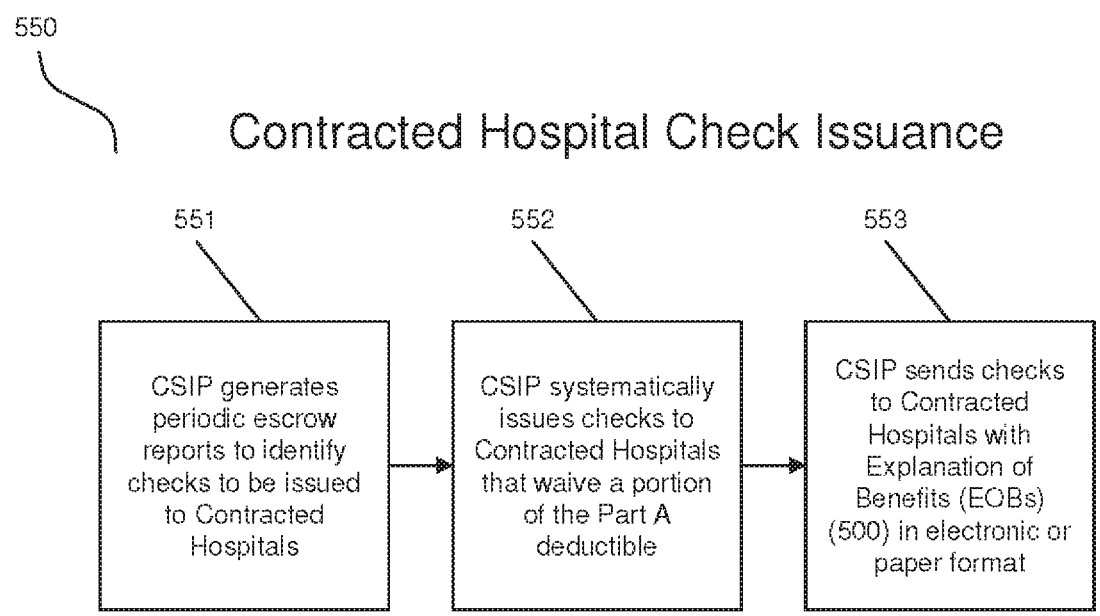
FIG. 8 depicts a flowchart of the check issuance process from a Contracted Supplemental Insurance Provider (CSIP) to a Contracted Hospital in accordance with the disclosed methods and systems.

Referring now to FIG. 8, the CSIP generates periodic escrow reports to identify checks that need to be issued to Contracted Hospitals (551). The CSIP systematically issues checks to Contracted Hospitals that waive a portion of the Part A Deductible (552). Checks are sent to Contracted Hospitals along with EOBs (500) in electronic or paper format (553).

Figure 9:
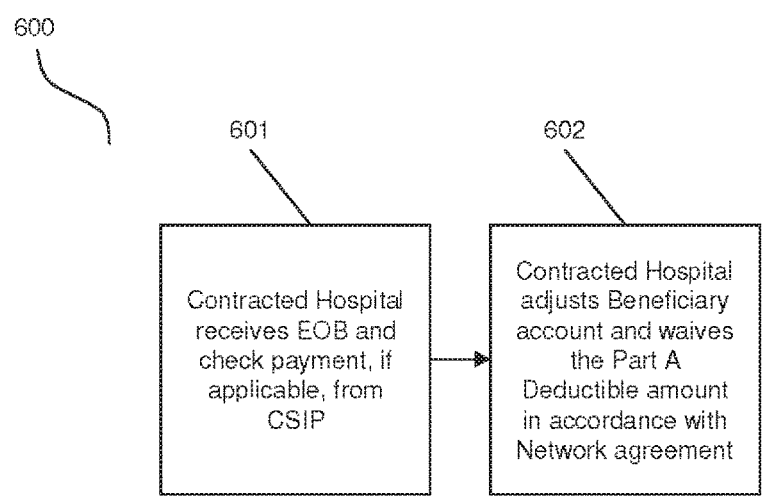
FIG. 9 depicts a flowchart showing the Contracted Hospital receiving an EOB in accordance with the disclosed methods and systems.

Referring now to FIG. 9, a Contracted Hospital receives an EOB, and payment if applicable, from the CSIP (601). The Contracted Hospital's billing staff processes the EOB and applicable payment and adjusts the patient account to reflect the Part A Deductible amount waived in accordance with their Network agreement (602).

Figure 10:
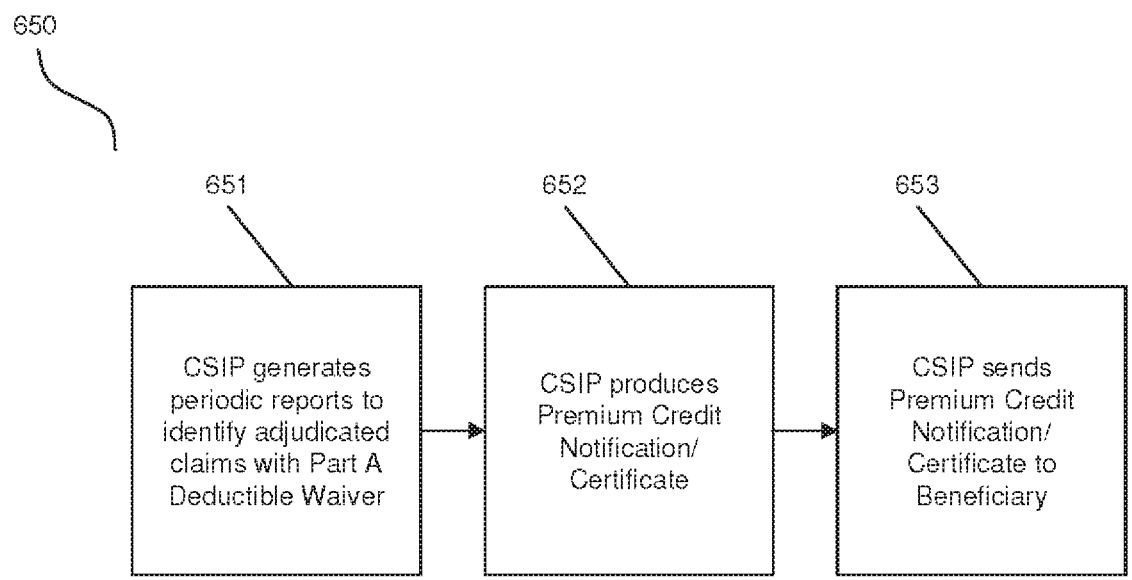
FIG. 10 depicts a flowchart of a premium credit being issued to a beneficiary in accordance with the disclosed methods and systems.

Referring now to FIG. 10, the CSIP generates periodic reports to identify adjudicated claims with Part A Deductible waived amounts (651). The CSIP queues its system to produce premium credit notification or certificates (652), an exemplar provided as FIG. 29. The CSIP sends the premium credit notification or certificate to Beneficiary to apply credit to their next premium payment to CSIP (653).

Figure 11:
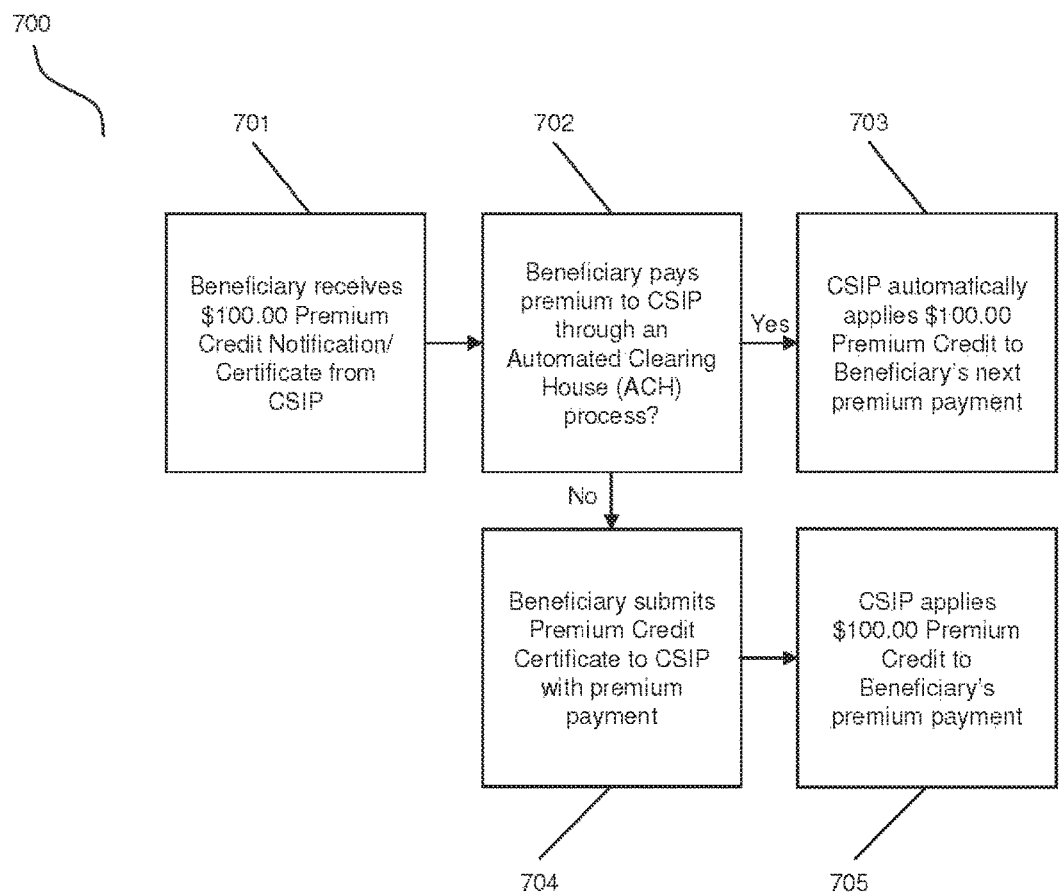
FIG. 11 depicts a flowchart of the beneficiary receiving notification of the premium credit in accordance with the disclosed methods and systems.

Referring now to FIG. 11, the Beneficiary receives the premium credit notification/certificate from the CSIP (701). For Beneficiary premium payments made based on an Automated Clearing House (ACH) transaction (702), the CSIP automatically applies the premium credit towards the next premium payment due from Beneficiary (703). For premium payments mailed to the CSIP by Beneficiaries, Beneficiary submits the premium credit certificate with their premium payment to the CSIP (704). The CSIP applies the premium credit upon receipt of Beneficiaries premium payment and premium credit certificate (705).

In an exemplary embodiment, insurance providers can send a monthly report (e.g., to a centralized network) detailing all deductibles incurred by their policyholders in the preceding months. A second report can be provided that is specific to all deductibles waived and payments made to contracted medical facilities. These reports can then be compared to one another, e.g., by a third party network representative, to avoid errors, omissions, and/or duplications, and to retain information for trending and analysis purposes. Retained information can include number of admissions by company, by state or other geographic region, and/or by month or other time period. Such information can also include the number of admissions to a contracted medical facility that were omitted from reports submitted by contracted insurance providers, the value of any non-utilized Part A waivers for the previous month and the identification of relevant medical facilities for refund requesting purposes, and/or the total number and location of all admissions to non-contracted medical facilities. The process for data reporting is referred to in FIGS. 12, 13, 13A, 14, 15, and 16.

Figure 12:
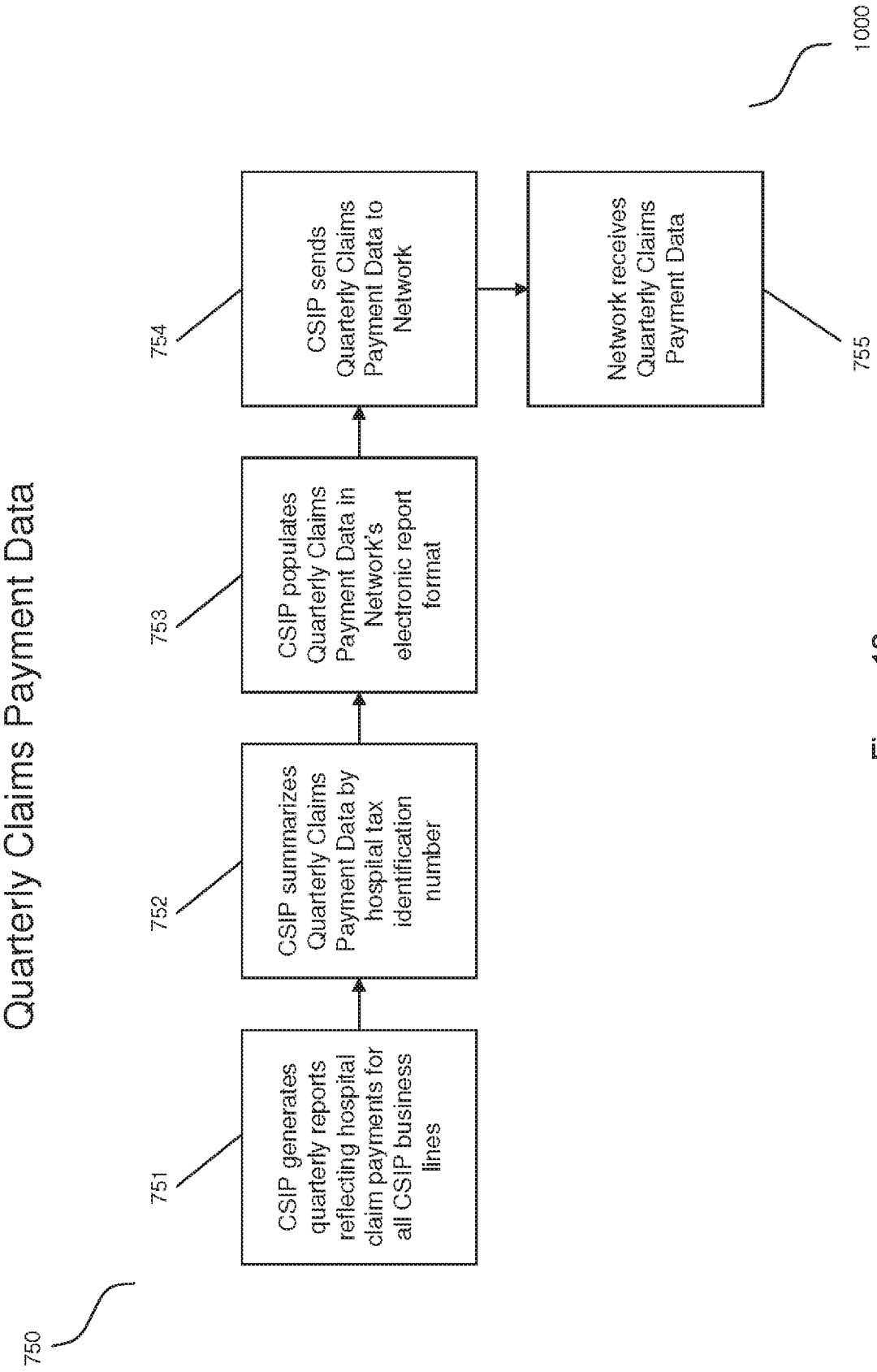
FIG. 12 depicts a flowchart showing the CSIP generating a quarterly claims payment statement in accordance with the disclosed methods and systems.

Referring now to FIG. 12, the CSIP generates quarterly reports reflecting hospital claim payments for all CSIP lines of business (751). The CSIP user logs in to claims adjudication system to access report menu for claims payment (1099 reporting), The user enters the quarterly timeframe for report selection with summarization by hospital tax identification number (752) and selects the option to generate the claims payment data requested. The user accesses the reported data and populates it in Network's electronic report format (753) (Refer to TABLE 2 for report template). The CSIP user uploads the quarterly claims payment data report on an established secure FTP site or sends to Network via secure email depending on CSIP reporting transmission setup (754).

TABLE 2

Report Template for Quarterly Facility Claims Payment Data

| File Date (M/Y) | Provider Data | | | | | Tax ID | NPI # | Claim Payment |
|---|---|---|---|---|---|---|---|---|
| | Name | Address | City | State | ZIP | | | |

Referring now to FIG. 16, the Network receives quarterly claims payment data (755) by downloading the report from an established secure FTP site or by secure email (756). Network stores quarterly claims payment data reports in original database format on system located on the network system and creates a working copy for processing (757). Network uploads quarterly claims payment report data into Network's quarterly claims payment database (758). Network aggregates data for all CSIP submitted reports (759). Network users may now generate database query reports on an ad-hoc basis for Network's medical facility marketing's use for developing the network of medical facilities resulting in executing contracts with medical facilities. The aggregated data is analyzed to determine the top utilized (paid) medical facilities by tax identification number. The top utilized medical facilities are most preferred by beneficiaries for seeking healthcare.

Figure 13:
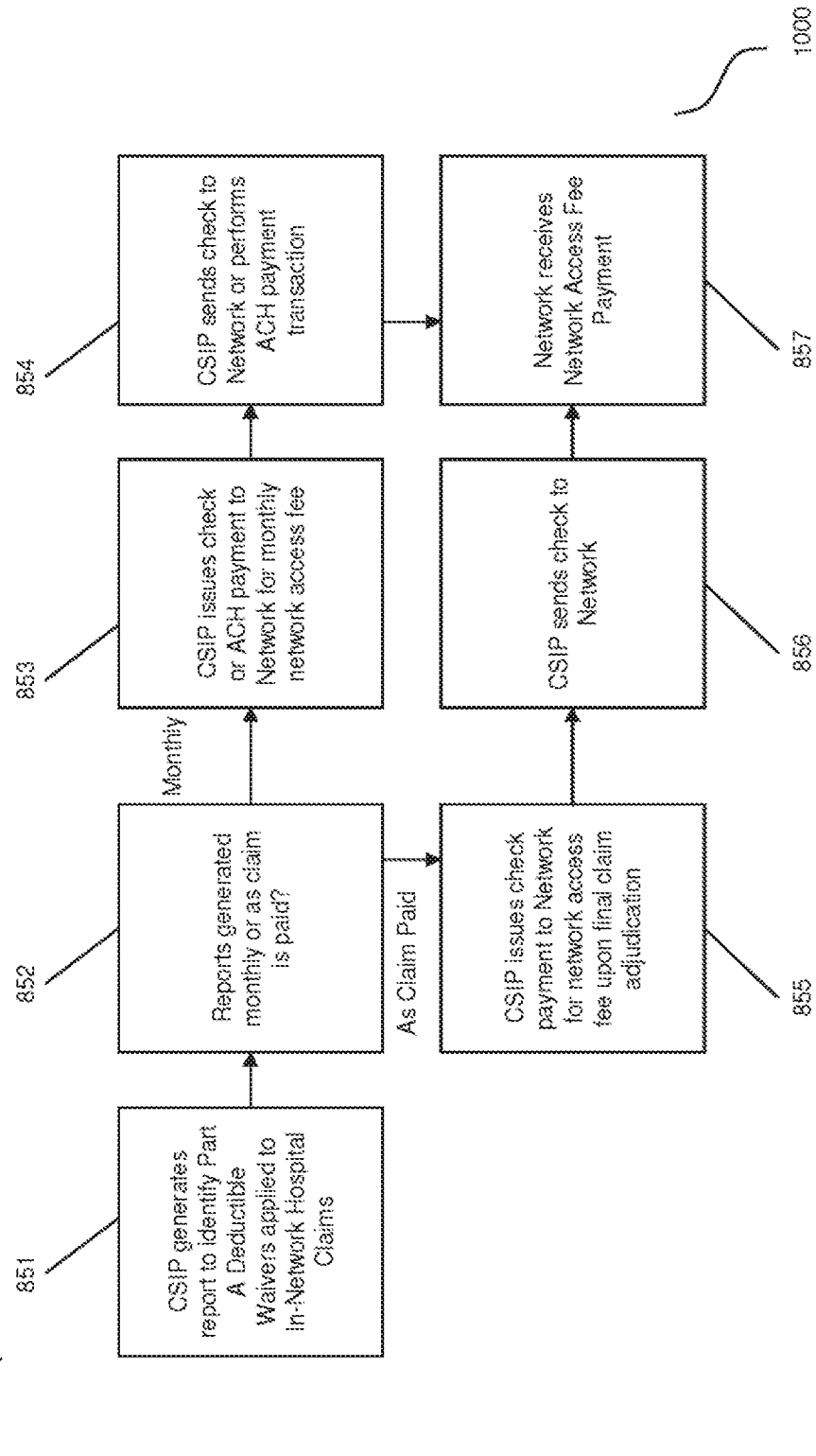
FIG. 13 depicts a flowchart of the CSIP paying an access fee to the Network in accordance with the disclosed methods and systems.
Figure 13A:
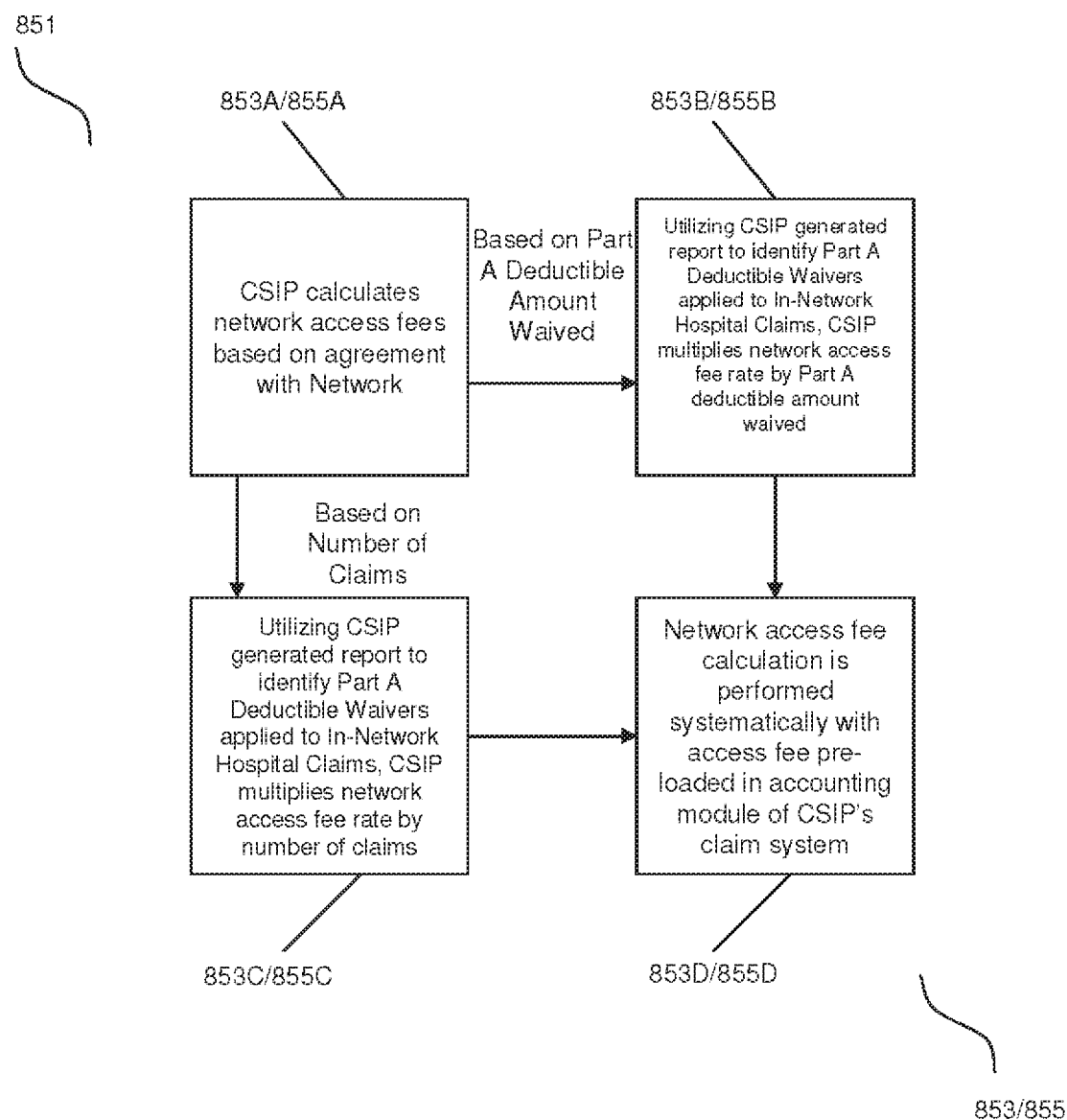
FIG. 13A depicts a flowchart of the CSIP network access fee calculation in accordance with the disclosed methods and systems.

Referring now to FIG. 13, the CSIP generates a report to identify Part A deductible waivers applied to Network participating medical facility claims and issues network access fee payments to Network (851). Referring specifically to FIG. 13A, CSIP calculates network access fees based on the established rate per the agreement by and between CSIP and Network (853A), (855A) as determined by an amount of increased revenue, an amount of decreased costs, or combinations thereof. Utilizing the computer generated report to identify Part A deductible waivers applied to In-Network Hospital claims (851), CSIP multiplies the established network access rate by the Part A deductible waived amount (853B), (855B). Or, CSIP multiplies the established network access fee rate by the number of claims a Part A deductible was applied (853C), (855C). This calculation processes are performed by the computer systematically through CSIP's programmed claims system with the network access fee pre-loaded in the accounting module of the claim system (853D), (855D). The CSIP issues payment for network access fees to Network on a per-claim or a monthly basis (852). For monthly payments, the CSIP user logs in to the claims adjudication system to access a report menu for claims processed with Part A deductible waivers. The CSIP user enters a monthly timeframe for report selection with claim details and selects the option to generate the claim data requested. The CSIP user accesses the reported data and submits a check request to issue payment for monthly network access fee to Network (853). The CSIP sends a check to Network or performs an ACH payment transaction (854). For payment on a per-claim basis, the CSIP's claims adjudication system is programmed to systematically issue a check for network access fee payment to Network upon final claim adjudication (855). The CRP sends a payment via check or ACH transaction check to Network (857).

Now referring to FIG. 16, Network receives network access fee payment from the CSIP (857). ACH transactions are systematically deposited into Network's designated bank account. Checks received by Network are deposited into Network's designated bank account by authorized user utilizing bank scanning software (858). Network applies credit to the CSIP account records (859).

Referring now to FIG. 14, the CSIP generates monthly reconciliation reports to identify all Part A admissions processed the prior month (901). CSIP user logs in to claims adjudication system to access report menu for adjudicated claims. CSIP user enters monthly timeframe for report selection with detail by claim and selects the option to generate the adjudicated claims requested. Depending on CSIP program system set-up, CSIP reports Part A waivers applied to participating medical facility claims (In-Network Hospital) along with non-participating medical facility claims (Non-Network Hospital) within the same report. CSIP reporting within the same report, CSIP user generates a reconciliation report detailing both In-Network and Non-Network Hospital Part A admissions (903). CSIP user accesses the reported data and populates it in Network's electronic report format (904) (Refer to TABLE 3 for report template). CSIP user uploads the monthly reconciliation report detailing both In-Network and Non-Network Hospital Part A admissions on an established secure FTP site or sends to Network via secure email depending on CSIP reporting transmission set-up (905).

TABLE 3

Monthly Network Utilization File Data Template

| Patient Data | | | | | | | |
|---|---|---|---|---|---|---|---|
| File Date (M/Y) | Claim # | First | Last | MI | Policy # | From DOS | To DOS |

| Provider Data | | | | | | |
|---|---|---|---|---|---|---|
| Name | Address | City | State | Zip | Tax ID | NPI # |

| Part A Deductible Paid to Facility | Part A Co-Pay/Ins. Paid to Facility | Fee Paid to Network |
|---|---|---|

Referring now to FIG. 16, Network receives monthly reconciliation report detailing both In-Network and Non-Network Hospital Part A admissions (910) by downloading the report from and established secure FTP site or by secure email (911). Network stores monthly reconciliation data reports in original database format on system located on the network system and also utilizes a working copy for processing (912). Network audits reconciliation report by matching In-Network Hospital Part A admissions to participating medical facility records in database. Network assigns unique identifying medical facility record numbers to each In-Network claim. Network separates In-Network Hospital Part A admissions and uploads monthly reconciliation report data into Network's Part A admission database (913). Network assigns unique identifying medical facility record numbers to each Non-Network claim if unique identifying medical facility record exists. Network uploads Non-Network Hospital Part A admissions into Network's Non-Network Hospital database (913).

Referring to FIG. 14, for CSIPs generating separate reports for In-Network Part A admissions and Non-Network Part A admissions, the CSIP user produces a reconciliation report detailing separately In-Network and Non-Network Hospital Part A admissions (906). The CSIP user accesses the reported data and populates it in Network's electronic report format, one report for In-Network Part A admissions and one report for Non-Network Part A admissions (907) (Refer to TABLE 3 & 4 for report templates). The CSIP user uploads both monthly reconciliation reports detailing In-Network and Non-Network Hospital Part A admissions on an established secure FTP site or sends to Network via secure email depending on the CSIP reporting transmission set-up (908). Network receives separate reports (909).

TABLE 4

Monthly Network Utilization File Data Template

| Provider Data | | | | | | | | |
|---|---|---|---|---|---|---|---|---|
| File Date (M/Y) | Name | Address | City | State | ZIP | Tax ID | NPI # | Medicare Admissions |

Network aggregates both In-Network and Non-Network data sets for utilization reporting (914). Network users may generate database query reports on a periodic basis for Network's medical facility marketing use for developing the network of medical facilities resulting in executing contracts with medical facilities. The aggregated data is analyzed to determine the top utilized medical facilities. The top utilized medical facilities are most preferred by beneficiaries for seeking healthcare. Thus, Non-Network facilities with high utilization profiles will be preferably sought by computer-based Network contracting analysis.

In an exemplary embodiment, this computer-based analysis (e.g., using a processor in communication with computer instructions) can additionally analyze the percentage of revenue associated with a selected group of insured patients, the extrapolated number of insured patients, other demographic and/or financial data, the number of reported admissions, and/or other data specific to a location, insurance policy, or group of patients.

Figure 23:
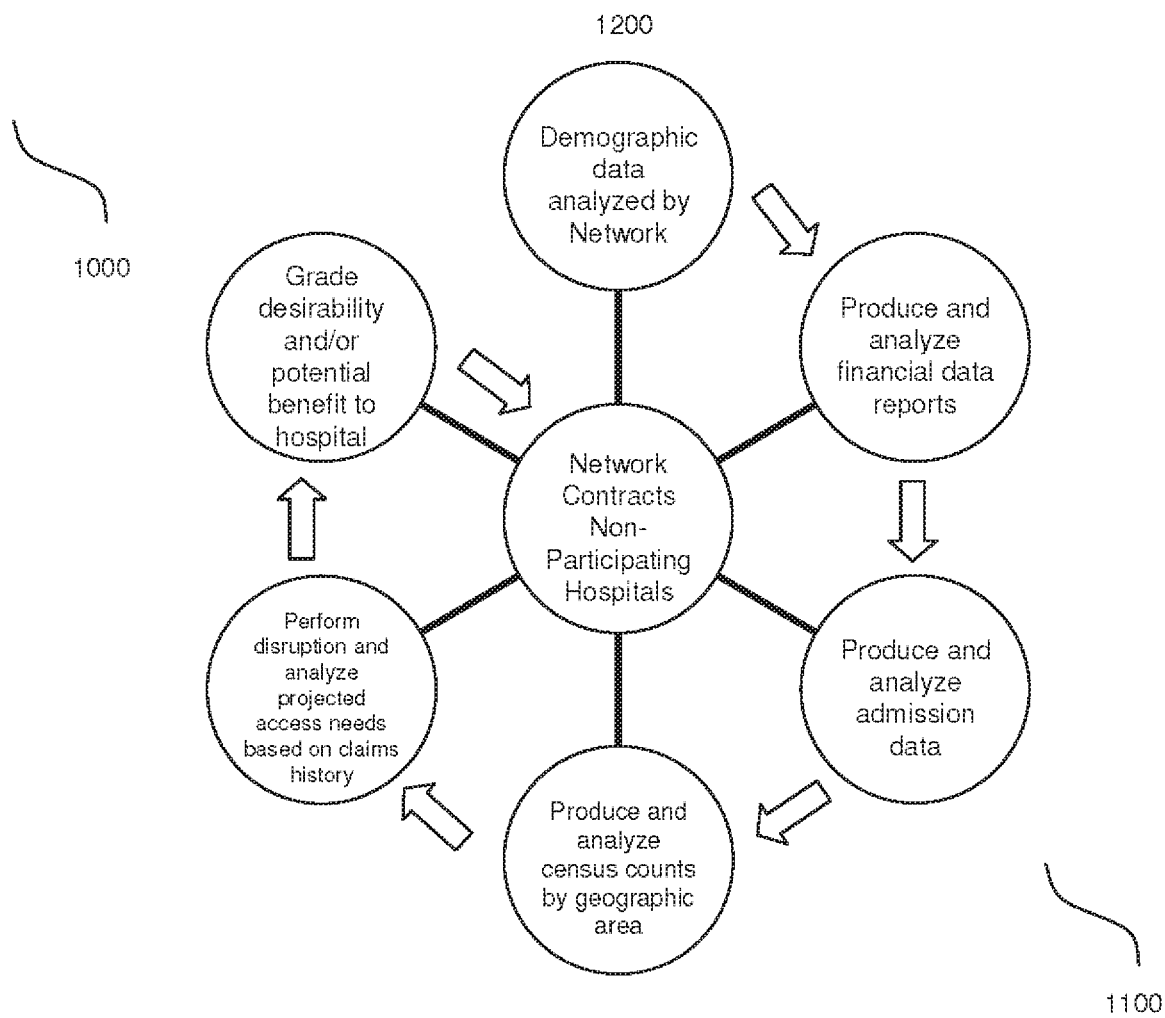
FIG. 23 depicts a flowchart of the Network contracting with a non-participating Hospital in accordance with the disclosed methods and systems

Referring specifically to FIG. 23, Network contracts with Non-Network hospitals and medical facilities in accordance with the disclosed methods and systems. This includes analyzing demographic data (FIGS. 16 & 19), producing and analyzing computer-implemented financial data reports (TABLE 5-6, FIG. 27-28), producing and analyzing admission data (FIG. 16), producing and analyzing census counts and geographic data (FIGS. 15 & 16), performing disruption analysis studies based on claim history (FIG. 19), grading desirability and/or potential benefit to hospitals (FIG. 28), and grading desirability based on physicians contracted with admitting privileges to hospital (FIG. 23A).

Figure 23A:
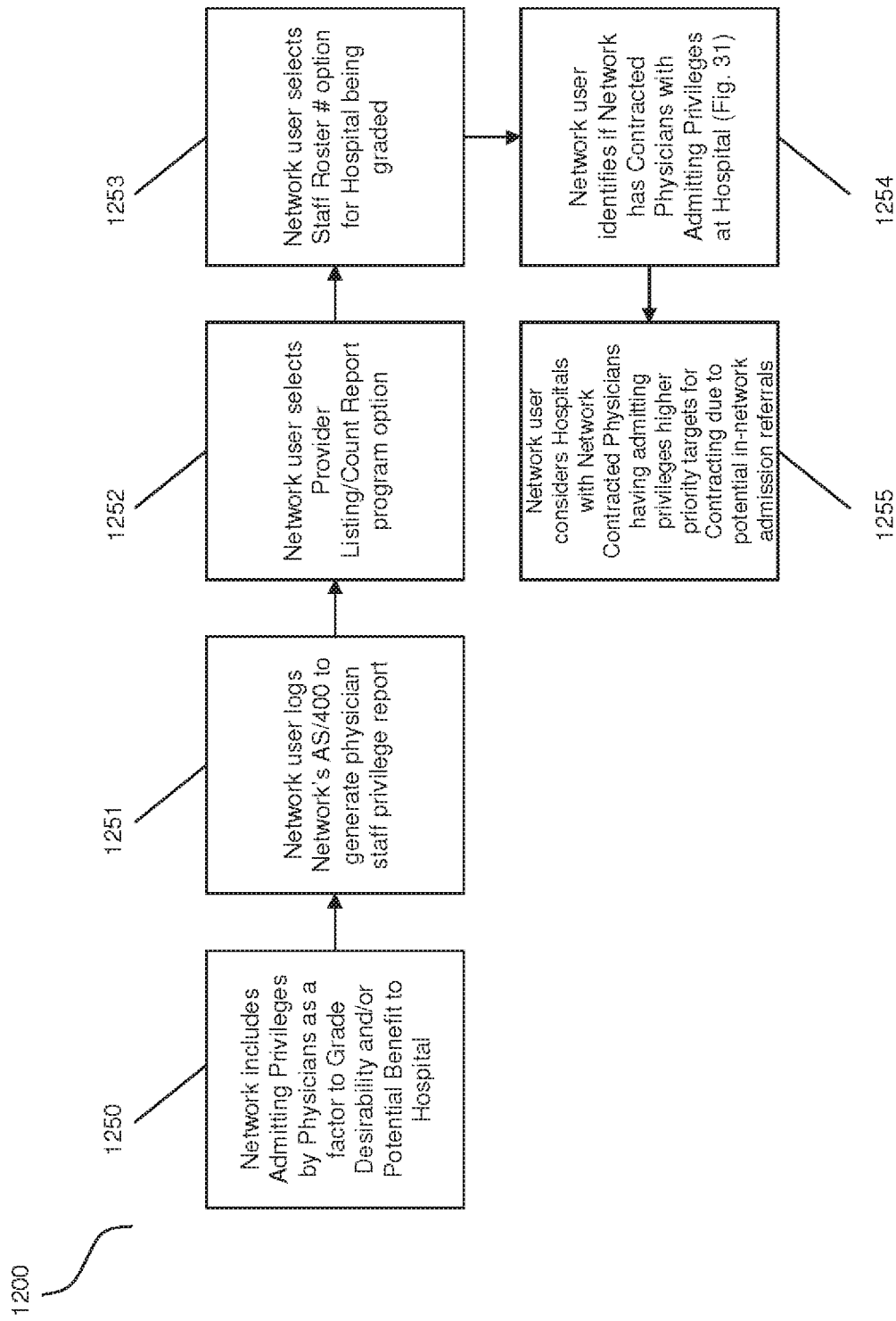
FIG. 23A depicts a flowchart of the Network grading desirability to contract with a non-participating Hospital in accordance with the disclosed methods and systems.

Referring specifically to FIG. 23A, admitting privileges by physicians is included as a factor to grade desirability and/or potential benefit to hospital (1250). Network user logs into Network's AS/400 system with user name and password to generate a physician staff privilege report (1251). Network user selects provider listing/count report program option (1252). Network user selects staff roster # option for hospital being graded (1253). Network user identifies if Network has contracted physicians with admitting privileges at hospital (1254). Network user considers hospitals with Network contracted physicians having admitting privileges higher priority targets for contracting hospitals due to potential in-network admission referrals (1255). Network generates, using the computer system, a template agreement used by Network to send to an identified Hospital or medical facility to contract and become a participating Network facility.

Figure 24:
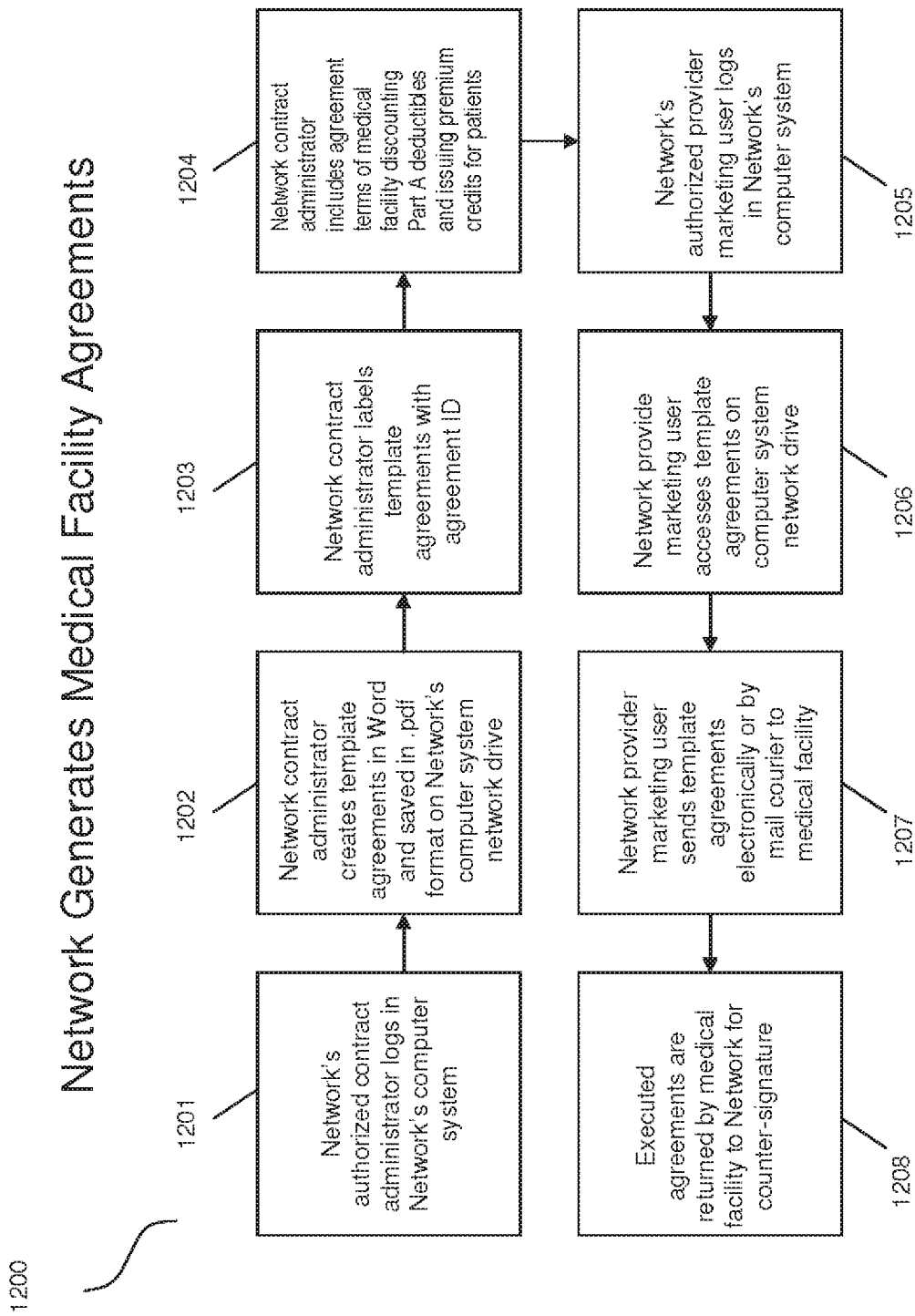
FIG. 24 depicts a flowchart of the Network generating medical facility agreements in accordance with the disclosed methods and systems.

Referring specifically to FIG. 24, Network's authorized contract administrator logs into Network's computer system with username and password (1201). Network contract administrator creates template agreements using Network's required contractual terms in Microsoft Word™ program and saves in Adobe Acrobat™ format on Network's computer system master contract network drive for Network provider marketing users' access (1202). Network's contract administrator labels template agreements with agreement ID based on agreement type, date, facility name, and computer system network path (1203). Template agreements include terms requiring medical facility to subtract at least a portion of a Part A deductible for a claim associated with an inpatient healthcare transaction and providing premium credits to insured patients in return (1204). Network's authorized provider marketing user logs into Network's computer system by entering username and password (1205). Network authorized provider marketing user then accesses template agreements on computer's master contract network drive (1206). Network authorized provider marketing user sends template agreements electronically or by standard mail courier to the identified loss leader medical facility along with a letter invitation to contract as a participating Network facility (1207). Executed agreements are returned by the medical facility electronically or by standard mail courier for Network's counter-signature by Network's authorized corporate officer (1208).

Figure 18:
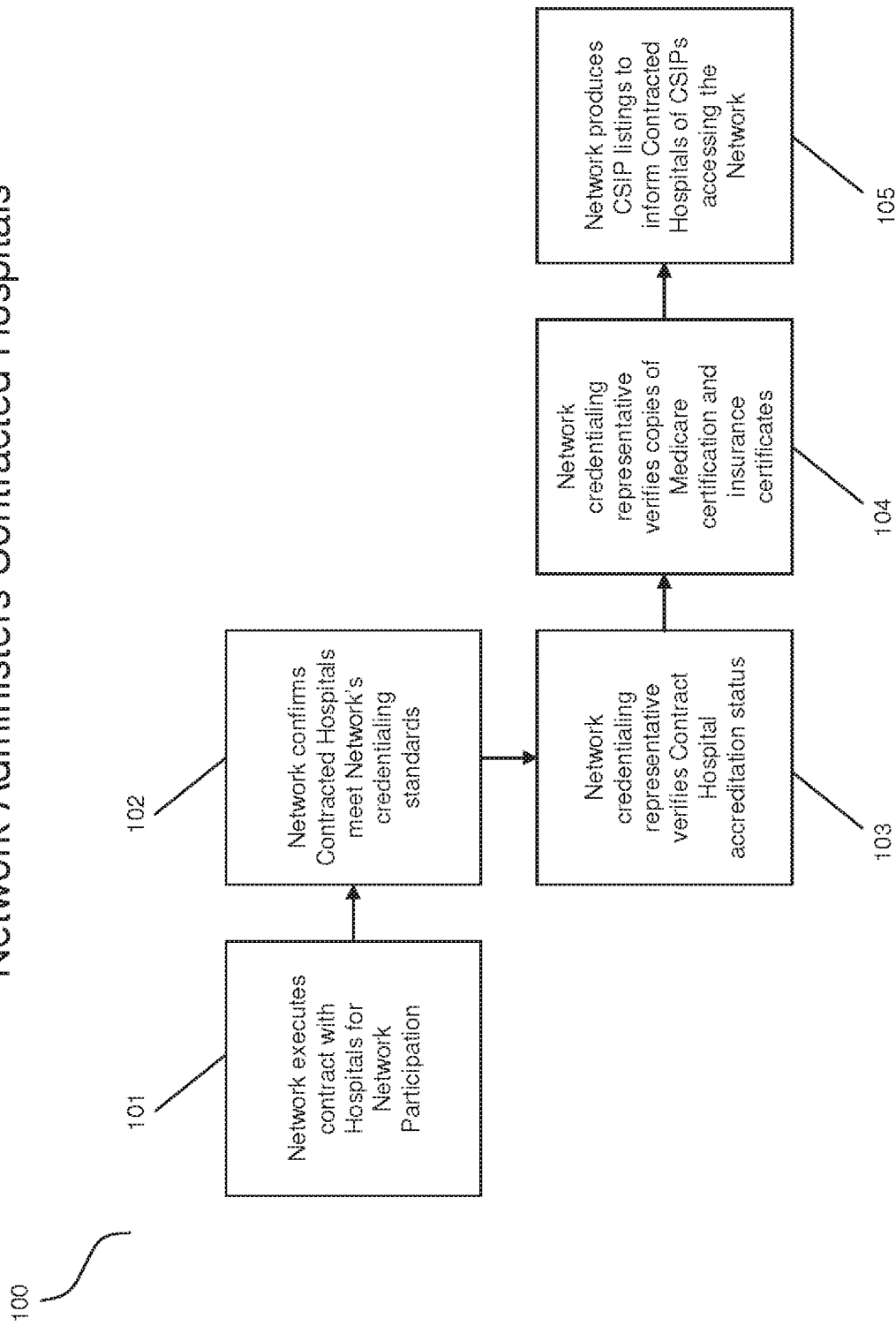
FIG. 18 depicts a flowchart of part of the Network administration process in accordance with the disclosed methods and systems.

Now referring specifically to FIG. 18, upon Network executing a contract with Hospital or medical facility (101), Network confirms Contracted Hospitals meet Network's credentialing standards (102). Network Contracted Hospitals must be accredited by The Joint Commission and/or be Medicare certified, carry malpractice and professional liability insurance, and maintain licenses and certifications required to meet state minimum requirements. Network credentialing representative logs into Network's computer system with username and password. Network credentialing representative verifies Contracted Hospitals Joint Commission accreditation by accessing the Internet. Network credentialing representative selects the tabs for Accreditation and Find a Healthcare Organization. Network credentialing representative performs search by organization name, zip code or by state to validate Contracted Hospital's accreditation status (104). A copy of the Contracted Hospital's Medicare certification and insurance certificate is received for Medicare certification and insurance validation (104). Network produces CSIP listings to inform Contracted Hospitals of CSIPs access the Network (105).

Figure 20:
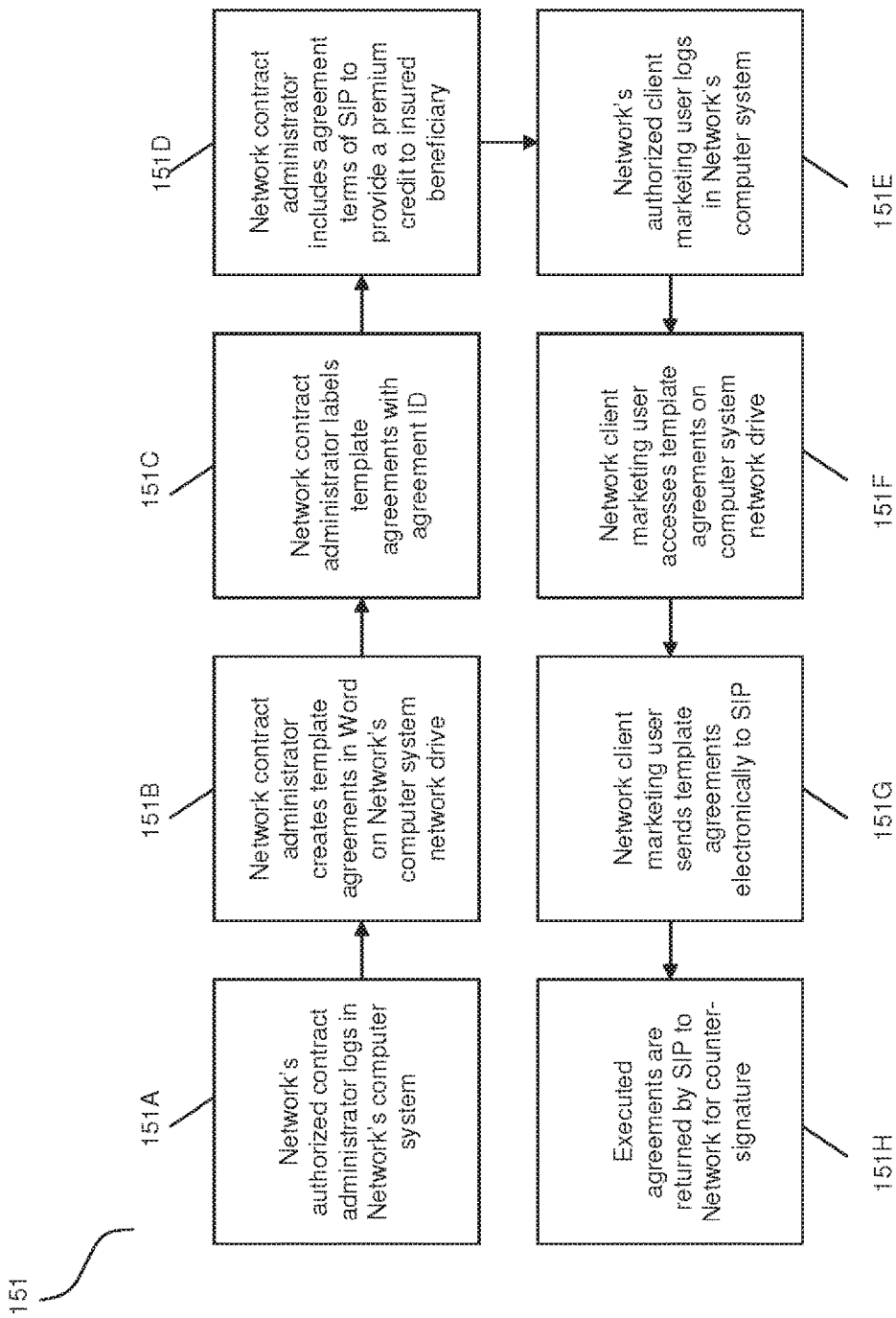
FIG. 20 depicts a flowchart of the Network generating supplemental insurance provider agreements in accordance with the disclosed methods and systems.

Referring specifically to FIG. 19, Network contracts with Supplemental Insurance Providers in accordance with the disclosed methods and systems. Network generates, using the computer system, a template agreement used by Network to send to a Supplemental Insurance Provider to contract and become a Contracted Supplemental Insurance Provider. Referring specifically to FIG. 20, Network's authorized contract administrator logs into Network's computer system with username and password (151A). Network contract administrator creates template agreements using Network's required contractual terms in Microsoft Word™ program and saves on Network's computer system master client contract network drive for Network client marketing users' access (151B). Network's contract administrator labels template agreements with agreement ID based on Network company name, Network department, agreement type, and Julian date (151C). Template agreements include terms requiring Supplemental Insurance Provider to provide a premium credit to insured beneficiary for an inpatient healthcare transaction that occurs at a Network Contracted Hospital that waives all or a portion of the Part A deductible (151D). Network's authorized client marketing user logs into Network's computer system by entering username and password (151E). Network authorized client marketing user then accesses template agreements on computer's master client contract network drive (151F). Network authorized client marketing user sends template agreements electronically or by standard mail courier to the identified Supplemental Insurance Provider along with a letter invitation to become a Contracted Supplemental Insurance Provider (151G). Executed agreements are returned by the Supplemental Insurance Provider electronically or by standard mail courier for Network's counter-signature by Network's authorized corporate officer (151H).

Referring specifically to FIG. 19, upon Network executing a contract with CSIP (151), Network implements contract by establishing a client record within Network's computer system (152). Network client representative logs into Network's computer system with username and password. Network client representative accesses Network client contractor/group system and creates a record in the computer system to track CSIP contract. Network provides file containing Contracted Hospitals to CSIP (250) (153). Network performs disruption analysis study of CSIP claims history to determine additional hospitals and medical facilities to contract (154).

CSIP implements contract with Network (155). CSIP sends claim history to Network for disruption analysis study (156). CSIP issues beneficiary ID cards with Network's name/logo (200) (157). CSIP provides Network with Office of Inspector General (OIG) advisory opinion request letter for approval (158). Upon Network's review and approval, CSIP sends OIG advisory opinion request letter to the Department of Health and Human Services (159). Upon receipt, CSIP provides Network with a copy of OIG Advisory Opinion issued by the Department of Health and Human Services OIG (160). On a bi-annual periodic basis, CSIP sends notices to existing beneficiaries explaining the advantages of using Contracted Hospitals (161).

Figure 21:
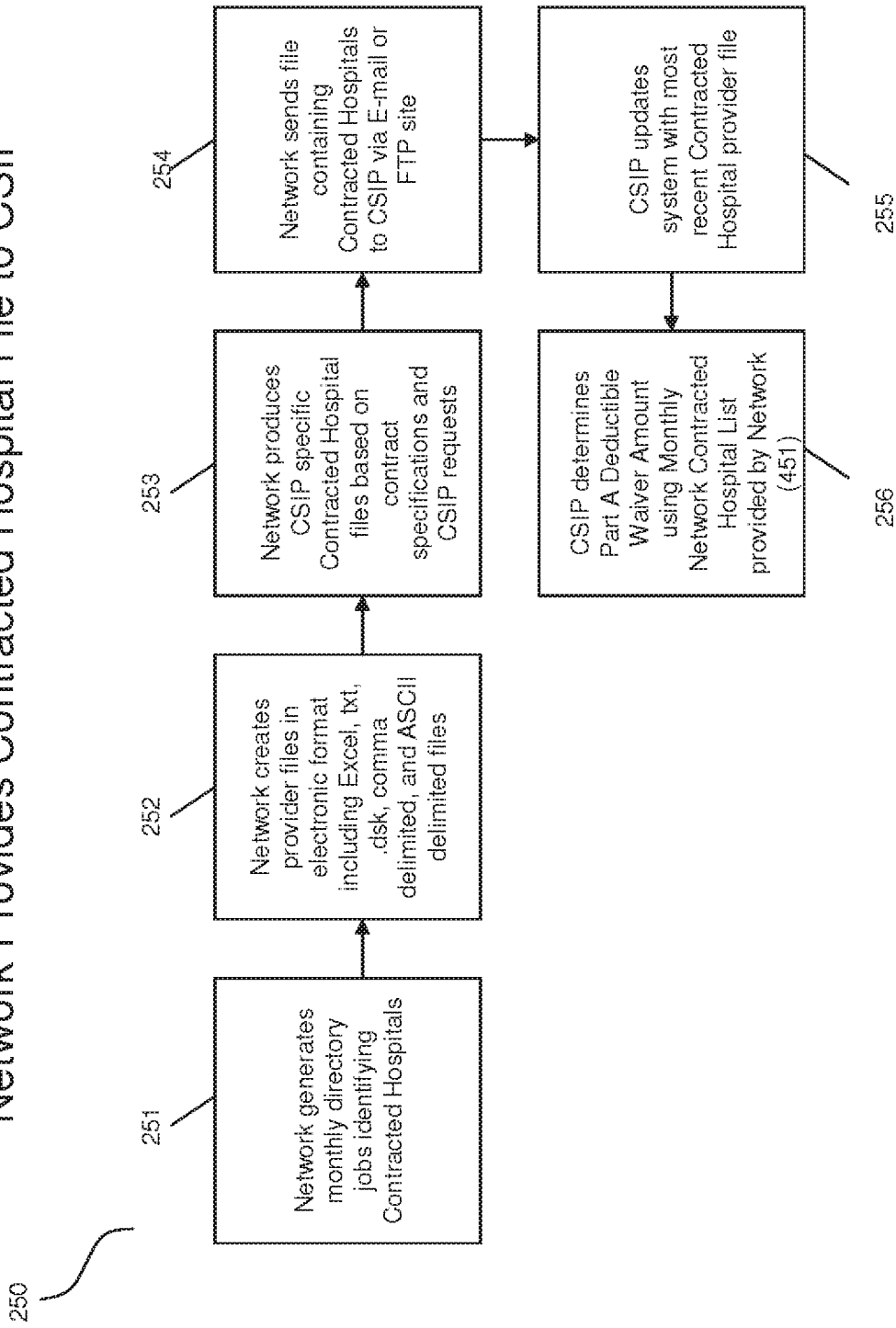
FIG. 21 depicts a flowchart of the Network providing files on the Contracted Hospitals to the CSIP in accordance with the disclosed methods and systems.

Now referring to FIG. 21, Network generates monthly directory jobs indentifying Contracted Hospitals (251). These are stored generated systematically through programmed robot jobs and SQL queries. Provider files are stored in electronic format including .xls, .txt, .dsk, comma delimited, and ASCII delimited files and (252). Network representatives utilize generated directory jobs to produce CSIP-specific Contracted Hospital files based on CSIP contracted specifications and requirements (253). Network sends Contract Hospital file to CSIP via secure e-mail or FTP site (254). CSIP receives Contracted Hospital file and updates computer system (255). CSIP determines Part A deductible waiver amount using monthly Network Contracted Hospital list provided by Network (451) (256).

Figure 22:
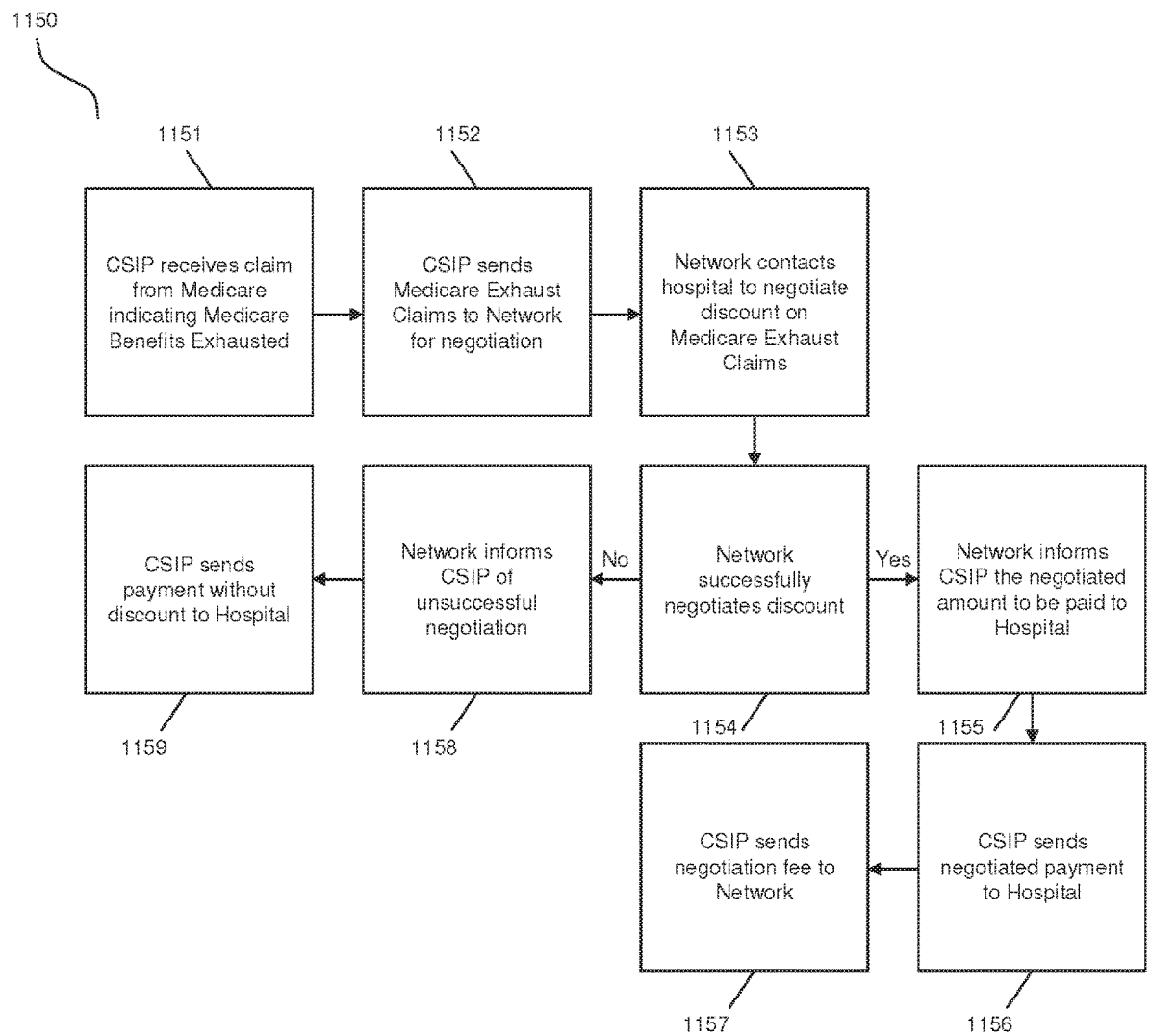
FIG. 22 depicts a flowchart of the Network negotiation process for a Medicare Exhaust Claim in accordance with the disclosed methods and systems.

Referring specifically to FIG. 22, Network negotiates discounts for CSIP Medicare exhaust claims. CSIP receives claim from Medicare indicating Medicare benefits have been exhausted for patient (1151). CSIP sends Medicare exhaust claim by secure e-mail or facsimile to Network for negotiation below the CSIP's pre-determined payment rate (1152). Network claims negotiation representative contacts hospital to negotiate Medicare exhaust claim (1153). Network determines if Medicare exhaust claims are negotiated successfully (1154). For successfully negotiated Medicare exhaust claim whereby a discount was negotiated below CSIP's pre-determined payment rate, Network negotiation representative informs CSIP the negotiated amount to be paid to hospital (1155). Upon CSIP approval, Network negotiation representative finalizes claim negotiation agreements with hospital and CSIP. CSIP sends negotiated payment to hospital (1156). CSIP sends negotiation fee to Network (1157). For unsuccessful Medicare exhaust claim negotiations, Network negotiation representative informs CSIP of unsuccessful negotiation (1158). CSIP sends pre-determined payment rate without discount to hospital (1159).

Figure 25:
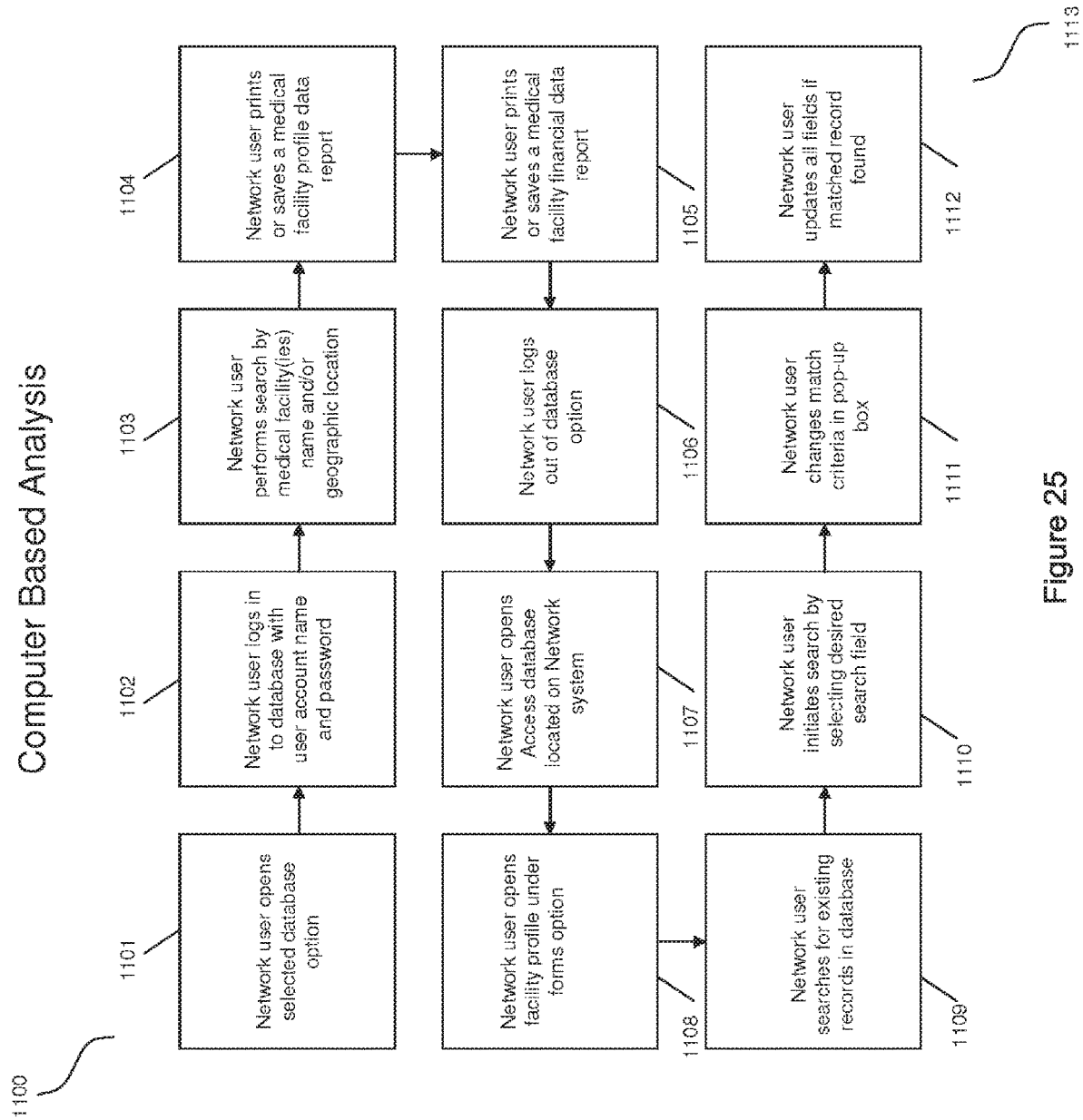
FIG. 25 depicts a flowchart of the computer-based analysis conducted by the Network in accordance with the disclosed methods and systems.
Figure 26:
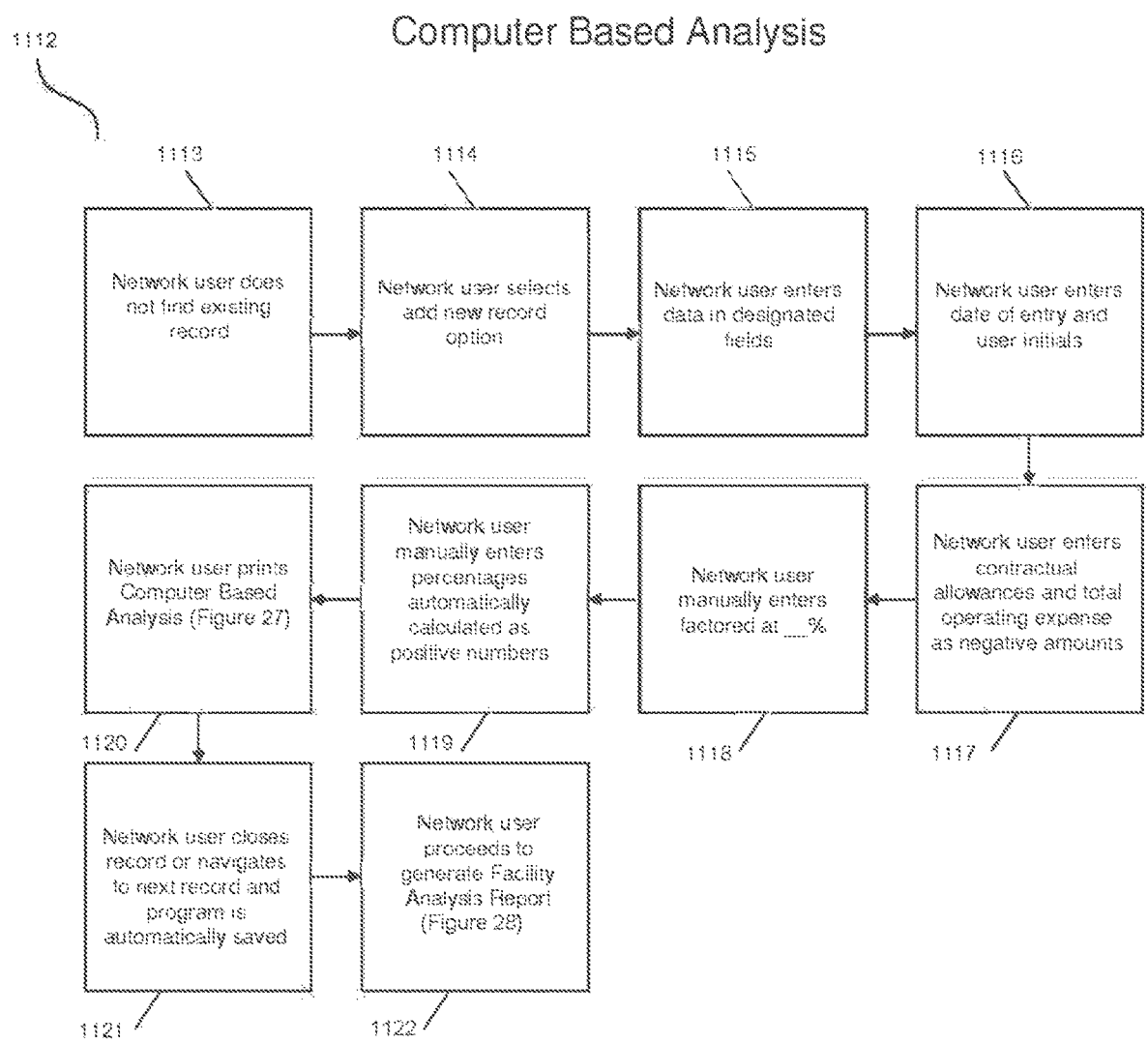
FIG. 26 depicts a flowchart of an entry of a new record into the database for computer-based analysis conducted by the Network in accordance with the disclosed methods and systems.

Referring specifically to FIG. 25, a Network user generates a computer-based analysis by performing the steps described in the following work flow (1100). The work flow begins by creating financial profile for a medical facility utilizing data sources described below. The user opens the selected database options (1101) and logs in to user account by entering user name and password (1102). User performs "search" for the specific medical facility by name and/or geographic location user desires to create such a financial profile (1103). User has the option to print or save the medical facility profile data report (1104), an exemplar of which is depicted as TABLE 5, and print or save the medical facility financial data report (1105), an exemplar of which is depicted as TABLE 6. User logouts of user account (1106). User opens database located on the system network at (1107). User opens facility profile under the forms option (1108). Before user adds new record(s) into database, user searches the database for an existing record by USA#, if one is available, or by using key words in the name field to prevent the creation of duplicate records of the same medical facility (1109). This is conducted by the user performing a search function on the field desired to be searched (1110). Within the pop-up box, user changes Match to "Any Part of Field" (1111). If user finds a match, then user simply updates all fields with current information, as applicable (1112). If a record is not found then user enters the information into a new record as depicted in FIG. 26 (1113).

TABLE 5

Exemplar Medical Facility Profile Data Report

Identification and Characteristics

| | |
|---|---|
| Type of Facility: Short Term Acute Care | Type of Control: Governmental, Other |
| General Med/Surg Beds: 474 | Special Care Beds: 78 |
| Total Employees: 3,614 | Total Discharges: 35,075 |
| Total Patient Days: 172,046 | Total Patient Revenue: $2,447,369,984 |
| County (FIPS Code): GA067—Cobb, GA | Longitude/Latitude: 85° E/34° N |
| Urban/Rural Designation: Urban | Medicare Certified Beds: 633 |

Acute Utilization Statistics by Payor

| | Beds | Revenue | Inpatient Days | | | |
|---|---|---|---|---|---|---|
| | | | Medicare | Medicaid | Other | Total |
| Routine Services | 474 | $176,490,592 | 51,545 | 6,026 | 75,127 | 132,698 |
| Intensive Care Unit | 54 | $38,514,432 | 6,493 | 1,691 | 7,226 | 15,410 |
| Coronary Intensive Care | 24 | $15,445,831 | 2,882 | 2,923 | 524 | 6,329 |
| Nursery | | $15,086,378 | N/A | 3,118 | 14,491 | 17,609 |
| Total Acute | 552 | $245,537,233 | 60,920 | 13,758 | 97,368 | 172,046 |
| Discharges | | | 11,209 | 2,850 | 21,016 | 35,075 |
| Average Length of Stay | | | 5.4 | 4.8 | 4.6 | 4.9 |
| Average Daily Census | | | 166.9 | 37.7 | 266.8 | 471.4 |

TABLE 5-continued

Exemplar Medical Facility Profile Data Report

Other Utilization Statistics by Payor

|  | Beds | Revenue | Medicare | Medicaid | Other | Total |
|---|---|---|---|---|---|---|
|  |  |  | Inpatient Days | | | |
| Rehabilitation Unit | 20 | $15,806,542 | 2,532 | 192 | 3,099 | 5,823 |
| Total Complex | 572 | $261,343,775 | 63,452 | 13,950 | 100,467 | 177,869 |
|  |  |  | Gross Patient Revenue | | | |
| Total Facility Revenue |  |  | $728,676,932 | $47,154,732 | $1,671,538,320 | $2,447,369,984 |

Estimated Patient Volumes

| Inpatient Surgeries: 12,600 | Outpatient Surgeries: 17,400 | Births; 7,400 |
|---|---|---|
| Outpatient Visits: 113,800 | ER (Not Admitted): 42,200 | ER (Admitted): 28,200 |

Clinical Services

Cardiovascular Services: Cardiac Cath Lab, Cardiac Rehab, Cardiac Surgery, Coronary Interventions,
Electrophysiology, Vascular Intervention, Vascular Surgery
Emergency Services, Emergency Department
Neurosciences: Electroencephalography (EEG)
Oncology Services: Cancer Program-ACS/CoC Approved, Chemotherapy, Radiation Therapy
Orthopedic Services: Joint Replacement, Spine Surgery
Other Services: Hemodialysis, Inpatient Surgery, Obstetrics
Radiology/Nuclear Medicine/Imaging: Computed Tomography (CT), Computed Tomography-Angiography
(CTA), Intensity-Modulated Radiation Therapy (IMRT), Magnetic Resonance Angiography (MRA), Magnetic
Resonance Imaging (MRI), Positron Emission Tomography (PET), Single Photon Emission Computerized
Tomography (SPECT)
Rehabilitation Services: Physical Therapy
Special Care: Coronary Intensive Care (CCU), Intensive Care Unit (ICU)
Subprovider Units: Rehabilitation
Wound Care

TABLE 6

Exemplar Medical Facility Financial Data Report

Balance Sheet

| Period Ending Date | Jun. 30, 2012 | Jun. 30, 2011 | Jun. 30, 2010 | Jun. 30, 2009 | Jun. 30, 2008 |
|---|---|---|---|---|---|
| Current Assets | $133,925,360 | $141,420,912 | $132,565,877 | $127,237,326 | $109,825,785 |
| Fixed Assets | $357,106,272 | $340,526,912 | $337,948,168 | $319,070,429 | $314,036,248 |
| Other Assets | $6,869,012 | $447,223,488 | $366,027,488 | $300,228,793 | $268,710,849 |
| Total Assets | $497,900,644 | $929,171,312 | $836,541,533 | $746,536,548 | $692,572,882 |
| Current Liabilities | $52,230,980 | $54,327,560 | $62,399,914 | $54,695,824 | $54,357,993 |
| Long-Term Liabilities | $240,169,584 | $248,796,576 | $292,592,955 | $270,190,373 | $229,822,909 |
| Total Liabilities | $292,400,564 | $303,124,136 | $354,992,869 | $324,886,197 | $284,180,902 |
| Total Fund Balances | $205,500,080 | $626,047,232 | $481,548,664 | $421,650,351 | $408,391,979 |
| Total Liabilities & Fund Balances | $497,900,644 | $929,171,368 | $836,541,533 | $746,536,548 | $692,572,881 |

Income Statement

| Period Ending Date | Jun. 30, 2012 | Jun. 30, 2011 | Jun. 30, 2010 | Jun. 30, 2009 | Jun. 30, 2008 |
|---|---|---|---|---|---|
| Inpatient Revenue | $1,283,337,728 | $1,223,520,640 | $1,106,493,902 | $986,157,292 | $930,250,571 |
| Outpatient Revenue | $1,164,032,256 | $969,422,528 | $894,936,450 | $775,620,264 | $678,251,250 |
| Total Patient Revenue | $2,447,369,984 | $2,192,943,168 | $2,001,430,352 | $1,761,777,556 | $1,608,501,821 |
| Contractual Allowance | $1,797,571,200 | $1,478,621,312 | $1,306,608,985 | $1,120,899,787 | $1,003,172,646 |
| Net Patient Revenue | $649,798,784 | $714,321,856 | $694,821,367 | $640,877,769 | $605,329,175 |
| Total Operating Expense | $574,617,472 | $650,410,944 | $633,611,942 | $580,286,918 | $556,440,653 |
| Depreciation Expense (included above) | $38,392,088 | $34,124,504 | $32,728,256 | $35,890,515 | $35,187,186 |
| Operating Income | $75,181,312 | $63,910,912 | $61,209,425 | $60,590,851 | $48,888,522 |
| Other Income | $0 | $0 | $0 | $0 | $0 |

TABLE 6-continued

Exemplar Medical Facility Financial Data Report

| | | | | | |
|---|---|---|---|---|---|
| Investment Income | $0 | $0 | $0 | $0 | $0 |
| Gov't Appropriations | $0 | $0 | $0 | $0 | $0 |
| Non-Patient Revenue | $11,794,295 | $11,618,062 | $4,493,907 | $11,937,894 | $14,780,580 |
| Total Other Expenses | $64,609 | -$39,232,992 | -$30,118,389 | $12,555,460 | $0 |
| Net Income/Loss | $86,910,998 | $114,761,966 | $95,821,721 | $59,793,285 | $63,669,102 |

Uncompensated Care

| | Revenue | Est. Cost |
|---|---|---|
| Medicaid | $238,638,352 | $53,433,272 |
| SCHIP | $3,407,881 | $763,055 |
| State/Local Indigent Care | $0 | $0 |
| Total Gov't Programs | $242,046,233 | $54,196,327 |
| Other Care | $177,794,032 | $39,809,684 |
| Restricted Grants | $0 | N/A |
| Unrestricted Grants | $0 | N/A |

Referring now to FIG. 26, user adds new record (1114). Starting from the top of the page, user begins entering data in the designated fields (1115). After entering the facility name, city/state and USA number, user will also enter the date of entry and user initials (1116). User follows the entry fields until user reaches "contractual allowances" and "total operating expense". These numbers are entered by user as negatives (1117). In the "factored at _____%" fields, user manually enters the percentage automatically calculated above in a decimal format, Example: 32% will be entered as 0.32, which will automatically display as a percentage when user tabs over to the next field (1118).

In the percentage income increase fields, user enters the percentages automatically calculated in spaces right below as positive numbers (1119). User prints the record by pressing the printer button at the top-left corner of the screen (1120). Records are automatically saved when user closes the record or navigates to a different record (1121).

Referring now to FIG. 27, an example of a generated facility financial profile report is illustrated. In the depicted embodiment, revenue, discharge, average length of stay (ALOS) and average daily censuses (ADC) are collected from the most recent reporting period of the facility profile report previously depicted as TABLE 6. In addition, the total value of new admissions are calculated from this data, and percentage income increases are projected for various scenarios of new admissions (e.g., 25, 50, 100 new patients) based on the revenue/discharge ratio. Referring back to FIG. 26, user proceeds to further utilize this information to generate Facility Analysis Report (1122).

Figure 30:
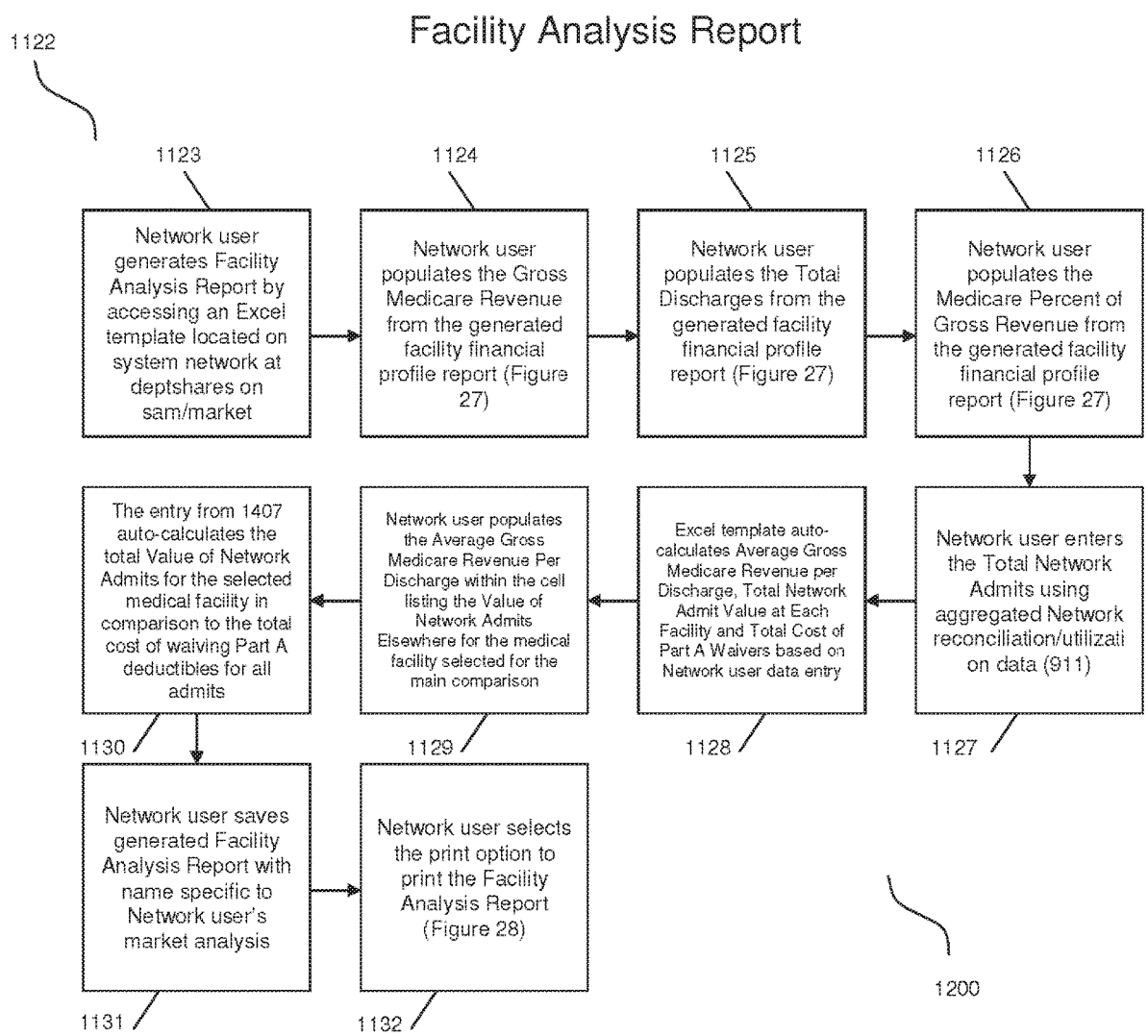
FIG. 30 depicts a flowchart of facility analysis reporting conducted in accordance with the disclosed methods and systems.

The Facility Analysis Report is generated in accordance with the methods depicted in FIG. 30. To create such a Facility Analysis Report, the user accesses an Excel™ template located on the system network (1123). The user populates the Gross Medicare Revenue (1124), Total Discharges (1125), and Medicare Percent of Gross Revenue (1126) from the facility financial profile report(s) for each medical facility to be included in the Facility Analysis Report comparison. Next, user enters the Total Network Admits for the time period of the comparison report for each medical facility using aggregated Network reconciliation/utilization data (909), (1127). The Facility Analysis Report Excel™ template auto-calculates the Average Gross Medicare Revenue Per Discharge, Total Network Admit Value at Each Facility, and Total Cost of Part A Waivers for each medical facility based on user entered data (1128). User populates the Average Gross Medicare Revenue Per Discharge within the cell listing the Value of Network Admits Elsewhere for the medical facility selected as the main comparison (1129). This entry auto-calculates the total Value of Network Admits for the selected medical facility in comparison to the total cost of waiving the Part A deductible for all admits (1130). User saves generated Facility Analysis Report with file name specific to Network user's market analysis (1131). User selects the print option to print the Facility Analysis Report (1132).

In the exemplar Facility Analysis Report, depicted as FIG. 28, Medical Center #2 is compared to various area Medicare facilities based the factors listed in the Financial Profile Reports. The Total Network Admits for the area are summed up as 780 and extrapolated to show the maximum possible revenue benefits experienced by Medical Center #2 in accordance with the disclosed methods and systems.

In addition to the data aggregated by the CSIP, data for these analyses may be obtained from various independent sources. Public use tiles can be obtained the U.S. Department of Health and Human Services, Centers for Medicare and Medicaid Services, consistent with CMS Data Release policies. Financial information from Medicare cost reports is maintained in cooperation with Cost Report Data Resources, an online source for cost report data. Information regarding Skilled Nursing Facilities is obtained in cooperation with SNFdata Resources, an online source for SNF cost report data and Medicare survey findings. The Healthcare Cost Report Information System (HCRIS) dataset contains the most recent version (i.e. as submitted, settled, reopened) of each cost report filed with CMS since federal FY 1996. The dataset consists of every data element included in the HCRIS extract created for CMS by a provider's fiscal intermediary. Cost reports are filed annually by hospitals according to their individual reporting years. This dataset is updated quarterly by CMS. The Medicare Provider Analysis and Review (MedPAR) file contains IPPS billing records for Medicare beneficiaries using hospital inpatient services. The MedPAR Limited Data Set (LDS) is based on discharges during the federal fiscal year ending September 30. A preliminary file is generally available in April after publication of the proposed PPS rule. A final file is generally available in early August after publication of the final PPS rule. (PPS rules are based on historical claims data from the fiscal year preceding their publication. For example, the rules for FY2011 are published in FY2010 using data from FY 2009.) The Hospital Outpatient Prospective Payment System (OPPS) Limited Data Set contains claim records for all Medicare beneficiaries using hospital outpatient services. The final file is usually provided by CMS about one month after publication of the OPPS final rule in late November.

The Medicare Provider of Services Listing contains identifying information for each Medicare provider. This information is updated quarterly by CMS. The Medicare Hospital Service Area File is derived by CMS from the calendar year inpatient claims data. The records contain number of discharges, length of stay, and total charges summarized by provider number and ZIP code of the Medicare beneficiary. This file is produced annually and is usually available in May. Hospital quality measurements are based on information from Hospital Compare, a website created through the efforts of the Centers for Medicare & Medicaid Services (CMS), an agency of the U.S. Department of Health and Human Services (DHHS) along with the Hospital Quality Alliance (HQA). Data are obtained quarterly or whenever the Hospital Compare website is updated. The National Plan and Provider Enumeration System (NPPES) collects identifying information on health care providers and assigns each a unique National Provider Identifier (NPI). A file containing NPIs and FOIA-disclosable data is obtained quarterly. Additionally, various proprietary and/or confidential data sources may be used.

The results of such an analysis can determine whether the expected increased revenue of a medical facility resulting from additional patient traffic resulting from the present methods and systems will exceed the cost associated with waiving all or a portion of the deductible amount. For example, if only a small percentage of a hospital's revenue is obtained through services provided to Medicare beneficiaries, but demographic data indicates a large number of individuals covered by Medicare supplemental policies are located in areas served by the hospital, the analysis may determine that the increased revenue generated by offering a premium credit and/or other incentives to patients covered by Medicare supplemental policies to utilize a specific medical facility will exceed the cost of waiving all or a portion of the Part A deductible amount for such patients.

Contracted insurance providers recognize increased revenue due to an increased number of enrolled beneficiaries, the beneficiaries being incentivized by the offered premium credits. For example, waiver of the $1,123 Medicare Part A deductible amount by a contracted hospital will more than offset the cost incurred by a contracted supplemental insurance provider when providing a $100 premium credit to a beneficiary. As described above, the total amount of premium credit provided to a beneficiary within a given time period can be limited (e.g., $600 per year). Waiver of the deductible amount enables claims from a contracted hospital and remittance from a contracted insurance provider to be repriced, and can further enable the premiums assessed by the insurance provider to be favorably adjusted.

Beneficiaries recognize increased savings through the provision of a premium credit from a contracted insurance provider, and through potentially reduced premiums made possible by the waiver of the deductible amount. In light of the reduction in transactional costs, contracted insurance providers may further adjust the premiums assessed to beneficiaries, enabling a larger number of beneficiaries to more readily afford desired policies.

The present embodiments thereby facilitate reduced expenses and increased revenues for beneficiaries, medical facilities, and insurance providers, while reducing the number of patients not covered by a Medicare supplemental insurance policy.

While the foregoing is directed to example embodiments of the disclosed invention, other and further embodiments of the invention may be devised without departing from the basic scope thereof, and the scope thereof is determined by the claims that follow.

What is claimed is:

1. A non-transitory computer readable recording medium storing a program to be executed on a computer, the program causing the computer to execute steps for forming a network for healthcare, comprising:

electronically receiving items of information about a plurality of medical facilities, each item of information including at least a name associated with an identification number and/or an address belonging to one of the plurality of medical facilities;

storing the items of information into a database;

determining whether an item of information stored in the database is from an in-network medical facility of the plurality of medical facilities found within the network, or is from an out-of-network medical facility of the plurality of medical facilities found outside of the network, wherein the determining comprises:

breaking down the name in the item of information into component words to determine whether each component word matches a word in a network name associated with one of the in-network medical facilities, and determining whether the identification number and/or the address associated with the name matches a network identification number and/or network address associated with one of the in-network medical facilities, wherein when the component words are at least 60% similar to the network name or its component words that are associated with one of the in-network medical facilities, and when the identification number and/or the address associated with the name is the same as the network identification number and/or the network address associated with the in-network medical facilities, the item of information is determined to be from an in-network medical facility; and when the component words are less than 60% similar to the network name or its component words associated with one of the in-network medical facilities, the determining further comprising breaking down the component words into component letters to determine whether the component letters match letters in the network name associated with one of the in-network medical facilities and determining whether the identification number and/or the address associated with the component letters matches the network identification number and/or the network address associated with one of the in-network medical facilities, wherein when the component letters are at least 90% similar to the letters in the network name and the identification number and/or the address associated with the component letters is the same as the network identification number and/or the network address associated with one of the in-network medical facilities, the item of information is determined to be from an in-network medical facility;

building a thesaurus look-up table by adding to the thesaurus look-up table at least one of a synonym, acronym and misspelling of at least one of the component words used in names in the items of information, and mapping the at least one of the component words to the at least one of the synonym, acronym and misspelling,
wherein the determining of whether each component word matches a word in the network name associated with one of the in-network medical facilities further comprises referring to the thesaurus look-up table to determine whether the component word matches at least one of the synonym, acronym and misspelling stored in the thesaurus look-up table, and wherein the determining of whether the component letters match the letters in the network name associated with one of the in-network medical facilities further comprises referring to the thesaurus look-up table to determine whether the component letters match letters of the at least one of the synonym, acronym and misspelling stored in the thesaurus look-up table, and
wherein when the component words are less than 60% similar to the network name or its component words and the component letters are less than 90% similar to the letters in the network name associated with one of the in-network medical facilities, the item of information is determined to be from an out-of-network medical facility;
storing results of the determining;
resolving whether a medical facility associated with an item of information that is determined to be from a medical facility that is outside of the network is to be included in the network, by assigning a value "X" to the medical facility, wherein the medical facility is included in the network when the value "X" is a positive number, and "X" is determined by the equation:

$$X=[(R+S)-(D*A)]/N$$

wherein "X" represents a monetary amount, "R" represents revenue due to increased patient admissions, "S" represents a monetary value of a payment from an insurance carrier, "D" represents a monetary amount of a deductible payment that is waived, "A" represents an adjusted revenue amount, and N represents a total number of new patient admissions, and
wherein "R" is calculated by the computer processor based on the computer processor's evaluation of: demographic data that predicts the number of medical facilities needed, financial data of the plurality of medical facilities to determine which revenue stream comes from each type of insurance accepted by the medical facilities, admission and discharge data to predict the number of insured patients within a geographic area, and physician data to apply a grade to physicians having admitting privileges;
adding to the network a medical facility having a value "X" that is a positive number;
waiving at least a portion of the deductible owed to the medical facility having a value "X" that is a positive number and that is added to the network, upon performance of the healthcare transaction by a member of a group of insured patients;
providing a premium credit to the member of the group of insured patients upon performance of the healthcare transaction with the medical facility having a value "X" that is a positive number and that is added to the network;
receiving a claim from the each respective member of the plurality of insurance providers;
re-pricing the claim by subtracting the at least a portion of the deductible; and
issuing the premium credit to the member of the group of the insured patients associated with the claim.

2. The non-transitory computer readable recording medium of claim 1, wherein the deciding step further comprises:
identifying a first number of reported admissions for each medical facility that is not in the network;
extrapolating, based on the identifying, a second number of the insured patients in order to predict a number of expected new patient admissions over a period of time at each medical facility that is not in the network;
evaluating demographic data to determine at least one location associated with the number of reported admissions;
evaluating financial data of each medical facility that is not in the network within said at least one location to determine a percentage of revenue associated with the group of insured patients; and
analyzing at least one of the percentage of revenue, the number of insured patients, the demographic data, the financial data, and the number of reported admissions, to determine a prospective result.

3. The non-transitory computer readable recording medium of claim 2, wherein the extrapolating the second number of insured patients using the first number of reported admissions comprises multiplying the first number by an inverse of an expected number of admissions per year for the insured patient.

4. The non-transitory computer readable recording medium of claim 3, wherein the expected number of admissions per year is approximately 0.26.

5. The non-transitory computer readable recording medium of claim 1, wherein the deciding step further comprises:
identifying, based on census data, each medical facility that is not in the network within a market area;
determining a percentage of revenue of each medical facility that is not in the network and that is associated with the group of insured patients;
determining, for each medical facility that is not in the network, at least one of an admission count and an average length of stay, associated with the group of insured patients; and
analyzing, for each medical facility that is not in the network, at least one of the percentage of revenue, the admission count, and the average length of stay, to determine whether the group of insured patients constitutes a loss leader for each medical facility that is not in the network.

6. The non-transitory computer readable recording medium of claim 5, further comprising subtracting said at least a portion of the deductible times an adjusted revenue amount from a sum of an expected revenue from increased admissions and a quantity of insurance payments to obtain a value.

7. The non-transitory computer readable recording medium of claim 6, further comprising dividing the value by a number of expected new patient admissions.

8. The non-transitory computer readable recording medium of claim 1, wherein the physician data comprises at least one of services offered and admitting privileges from specialty physicians.

9. The non-transitory computer readable recording medium of claim 1, wherein the deciding step further comprises:

identifying, based on a medical facility profile, revenue, discharge, average length of stay, and average daily census for each medical facility that is not in the network, a projected value for new admissions; and conducting, based on a plurality of facility profiles in a geographic area, a facility analysis based on a maximum projected number of network admits in area medical facilities.

10. The non-transitory computer readable recording medium of claim 1, wherein the deciding step further comprises:

identifying a number of beneficiaries, claim payments, admissions, or combinations thereof, using data sets for at least one insurance provider in an area; and aggregating the data sets for a utilization report determining the most utilized medical facilities.

11. The non-transitory computer readable recording medium of claim 1, wherein re-pricing the claim further comprises re-pricing the cost of a policy based on a notification issued to the plurality of insurance providers.

12. The non-transitory computer readable recording medium of claim 1, wherein the program further causes the computer to identify at least one insurance provider that requires additional contracting of medical facilities, by conducting at least one of claims analysis history, disruption study, and census count.

13. The non-transitory computer readable recording medium of claim 1, wherein the program further causes the computer to periodically provide a list of in-network medical facilities to the insurance providers, periodically provide a list of insurance providers to an in-network medical facility, or combinations thereof.

14. The non-transitory computer readable recording medium of claim 1, wherein the program further causes the computer to request collection of a fee from each in-network medical facility, the plurality of insurance providers, or combinations thereof, wherein the fee is determined by at least one of an amount of increased revenue and an amount of decreased costs.

15. The non-transitory computer readable recording medium of claim 1, wherein the plurality of insurance providers comprises Medicare supplemental insurance providers, and the deductible comprises a Medicare Part A deductible.

16. The non-transitory computer readable recording medium of claim 1, wherein the plurality of medical facilities comprises at least one of a hospital, skilled nursing facility, home healthcare provider, hospice, bariatric surgery facility, chemical dependency center, long-term care facility, physical rehabilitation center, psychiatric facility, residential treatment center, sub-acute facility, medical practitioner, and group of medical practitioners.

17. The non-transitory computer readable recording medium of claim 1, wherein the network is invisible to the insured patients.

* * * * *